(12) United States Patent
Heislop et al.

(10) Patent No.: US 11,864,860 B2
(45) Date of Patent: Jan. 9, 2024

(54) BIOMETRIC IMAGING AND BIOTELEMETRY SYSTEM

(71) Applicants: Christian Heislop, Crossville, TN (US); Joseph Swift, Crossville, TN (US)

(72) Inventors: Christian Heislop, Crossville, TN (US); Joseph Swift, Crossville, TN (US)

(*) Notice: Subject to any disclaimer, the term of this patent is extended or adjusted under 35 U.S.C. 154(b) by 389 days.

(21) Appl. No.: 17/338,866

(22) Filed: Jun. 4, 2021

(65) Prior Publication Data

US 2022/0079439 A1 Mar. 17, 2022

Related U.S. Application Data

(60) Provisional application No. 63/119,856, filed on Dec. 1, 2020, provisional application No. 63/077,985, filed on Sep. 14, 2020.

(51) Int. Cl.
| | |
|---|---|
| *A61B 5/02* | (2006.01) |
| *G16H 50/80* | (2018.01) |
| *A61B 5/00* | (2006.01) |
| *G16H 15/00* | (2018.01) |
| *G16H 10/60* | (2018.01) |

(Continued)

(52) U.S. Cl.
CPC .......... *A61B 5/0013* (2013.01); *A61B 5/0008* (2013.01); *A61B 5/0077* (2013.01); *A61B 5/01* (2013.01); *G16H 10/60* (2018.01); *G16H 15/00* (2018.01); *G16H 30/40* (2018.01);

(Continued)

(58) Field of Classification Search
USPC ............... 382/100–128, 154–227; 706/1–62, 706/900–903
See application file for complete search history.

(56) References Cited

U.S. PATENT DOCUMENTS

| 9,419,951 B1 | 8/2016 | Felsher |
| 11,587,048 B2 * | 2/2023 | Kang .................... G06Q 20/308 |

(Continued)

OTHER PUBLICATIONS

Khatri Purvesh, Methods for Diagnosis of Sepsis, Sep. 2016 (Year: 2016).*

(Continued)

*Primary Examiner* — Marcellus J Augustin
(74) *Attorney, Agent, or Firm* — Blanchard Horton PLLC

(57) ABSTRACT

A biometric imaging and biotelemetry (BIB) system is provided that may be configured to capture, analyze, and process qualitative and quantitative biomarker data acquired from the process of imaging individuals. The BIB system can rapidly measure facial and other body temperatures of a test subject, along with a plurality of other biometric parameters that may be compiled into a subject-specific health profile which, in turn, may provide insights into the wellness or illness of the individual. The BIB system captures biometric data by appropriately configured, multispectral, high resolution digital cameras and sensors. This data is then interconnected to data processing units that employ algorithms, artificial intelligence, and self-learning/deep learning to analyze and process data, render decisions, and manage actions via complex analytical methodologies. The BIB system provides essentially instantaneous analyses that give real-time insights into the wellness or illness of a test subject.

20 Claims, 17 Drawing Sheets

(51) Int. Cl.
    *G16H 30/40* (2018.01)
    *A61B 5/01* (2006.01)
    *G16H 50/70* (2018.01)
    *H04N 23/56* (2023.01)
    *H04N 23/90* (2023.01)

(52) U.S. Cl.
    CPC ............ *G16H 50/70* (2018.01); *H04N 23/56* (2023.01); *H04N 23/90* (2023.01)

(56) References Cited

U.S. PATENT DOCUMENTS

| | | | |
|---|---|---|---|
| 2009/0062624 A1* | 3/2009 | Neville | G16H 50/20 600/300 |
| 2012/0172679 A1* | 7/2012 | Logan | A61B 5/6803 600/301 |
| 2015/0049163 A1* | 2/2015 | Smurro | H04L 65/403 348/14.08 |
| 2018/0137244 A1 | 5/2018 | Sorenson et al. | |
| 2019/0206546 A1 | 7/2019 | Shneemann | |
| 2019/0361002 A1 | 11/2019 | Chou et al. | |
| 2020/0214649 A1 | 7/2020 | Cogley | |
| 2020/0244716 A1 | 7/2020 | Mehta et al. | |
| 2020/0245873 A1 | 8/2020 | Frank | |
| 2020/0253562 A1 | 8/2020 | Newberry et al. | |
| 2020/0273578 A1 | 8/2020 | Kutzko et al. | |
| 2020/0279339 A1 | 9/2020 | Akutagawa et al. | |
| 2020/0323484 A1 | 10/2020 | Aronovich et al. | |
| 2020/0334379 A1 | 10/2020 | Derosa-Grund | |
| 2020/0372743 A1 | 11/2020 | Miller et al. | |
| 2020/0397306 A1 | 12/2020 | Frank et al. | |
| 2021/0313077 A1* | 10/2021 | Smurro | G16H 50/20 |
| 2022/0079439 A1 | 3/2022 | Heislop | |

OTHER PUBLICATIONS

Tsuda K., Portable Biometric Information Recording Device Of Biotelemetry System For Measuring And Recording Biometric Information, Has Recording Unit Which Records Measured Heart Rate, Position And Temperature Information; Jan. 2014 (Year: 2014).*

* cited by examiner

| | Category | Head and/or facial image effecting factor |
|---|---|---|
| 1350 | permanent | moles, hairy moles, scars, pimples, acne |
| 1360 | removable | mask on face |
| | removable | caps, hats, scarfs, turbans, turtle necks, hoodies, etc. |
| | removable | eye glasses, sun glasses |
| | removable | hand covering face |
| | removable | dirt on face, rain, & wet |
| 1370 | noise | open/closed mouth |
| | noise | facial hair (beards, mustaches, side-burns.) |
| | noise | long hair (bangs, hair wrapped over face, ears, etc.) |
| | noise | lipstick (different colors and glosses) |
| | noise | jewelry, nose rings, eyelid rings, studs, etc. |
| | noise | uncontrolled motion (spastic, nervous, etc.) |
| | noise | talking on cell phone within the field of view |
| | noise | eating, chewing |
| | noise | ambient audio noise, background music, construction, conversations |
| | noise | shading and shadows (natural light) |

FIG. 13

| Index # | | Category | BIOMARKER Parameter (description) | Variable code |
|---|---|---|---|---|
| 1 | 1591 | Thermal | Temp max | Tmax |
| 2 | | Thermal | Temp min | Tmin |
| 3 | | Thermal | T max - T min | delta T |
| 4 | | Thermal | Ambient Ts (T1)1st entry | TE1 |
| 5 | | Thermal | Ambient (T2) intermediate | TE2 |
| 6 | | Thermal | Ambient (T3) final | TE4 |
| 7 | 1592 | Colorimetric | color left eye | CLE |
| 8 | | Colorimetric | color right eye | CRE |
| 9 | | Colorimetric | color upper lip | CUL |
| 10 | | Colorimetric | color lower lip | CLL |
| 11 | | Colorimetric | color nose (left side) | CNL |
| 12 | | Colorimetric | color nose (right side) | CNR |
| 13 | | Colorimetric | color nose (center) | CNC |
| 14 | | Colorimetric | color left eye | CLE |
| 15 | | Colorimetric | color density right eye | CDER |
| 16 | | Colorimetric | color density upper lip | CDLU |
| 17 | | Colorimetric | color density lower lip | CDLL |
| 18 | | Colorimetric | color density nose (left side) | CDNL |
| 19 | | Colorimetric | color density nose (right side) | CDNR |
| 20 | | Colorimetric | color density nose (center) | CDNC |
| 21 | 1593 | Dimension | width (max) nose | WN |
| 22 | | Dimension | position of lower left eyelid | PLEL |
| 23 | | Dimension | position of upper left eyelid | PUEL |
| 24 | | Dimension | left eyelid opening | delta PUL -PLEL |
| 25 | | Dimension | position of lower right eyelid | PLRL |
| 26 | | Dimension | position of upper right eyelid | PUEL |
| 27 | | Dimension | right eyelid opening | delta PURL - PLRL |
| 28 | 1594 | Rate | left eye blink rate | d EL/dt |
| 29 | | Rate | right eye blink rate | d ER/dt |
| 30 | | Rate | blink latency | t BL |
| 31 | 1595 | Topographic | coordinates of reference point 1 | X1,Y1 |
| 32 | | Topographic | polar coordinates of reference point 1 | xx1, angle 1 |
| 33 | | Topographic | coordinates of reference point 2 | X2,Y2 |
| 34 | | Topographic | polar coordinates of reference point 2 | xx2, angle 2 |
| 35 | | Topographic | coordinates of reference point 3 | X3, Y3 |
| 36 | | Topographic | polar coordinates of reference point 3 | xx3, angle 3 |
| 37 | 1596 | Reflexologic | latency (1) wrt audio stimulus | L (1) |
| 38 | 1594 | Rate | delta (X1, Y1) to undefined external point | d X1, Y2/dt |
| 39 | 1595 | Reflexologic | lag time at undefined external point | t S |
| 40 | 1594 | Rate | delta undefined external point upon return to (X1, Y1) | L (2) |

| CONDITION | Probability (%) | Confidence level (%) |
|---|---|---|
| viral infection, flu, COVID, cold | 92% | 90 |
| stroke | <10 | 90 |
| poraliasis | <10 | 90 |
| autoimmune vasculitis | 86 | 90 |
| Graves' disease | <10 | 90 |
| Myasthenia gravis | <10 | 90 |

FIG.16

| Description of Parameters Employed | Variable code |
|---|---|
| maximal facial temperature | Tmax |
| minimal facial temperature | Tmin |
| difference (Tmax - Tmin) | dT |
| rate of facial temperature change | dT/dt |
| surrounding room temperature | TE1 |
| color nose (left side) | CNL |
| color nose (right side) | CNR |
| color nose (center) | CNC |
| color density upper lip | CDLU |
| color density lower lip | CDLL |
| color density nose (left side) | CDNL |
| color density nose (right side) | CDNR |
| color density nose (center) | CDNC |
| width (max) nose | WN |
| left eye blink rate | d EL/dt |
| right eye blink rate | d ER/dt |
| blink latency | t BL |

FIG.17

BIOMETRIC IMAGING AND BIOTELEMETRY SYSTEM

REFERENCE TO RELATED APPLICATIONS

This application claims the benefit of U.S. Provisional Patent Application No. 63/077,985 entitled "Biometric Imaging and Biotelemetry System" filed on Sep. 14, 2020, and U.S. Provisional Patent Application No. 63/119,856 entitled "Biometric Imaging and Biotelemetry System" filed on Dec. 1, 2020, each of which is incorporated herein by reference in its entirety.

BACKGROUND

Thermal imaging cameras and devices are widely used to measure the facial temperature-profiles of test subjects suspected of being infected with a disease such as the Coronavirus Disease 2019 (COVID-19). These thermal imaging cameras and devices typically operate in the InfraRed (IR) electromagnetic spectrum to measure the facial temperature-profiles of the test subjects. Facial temperatures alone generally are not recognized to function as a predictor of COVID-19 or of any illness. However, more accurate and precise methods are not routinely available where and when needed to determine whether a test subject is infected with a disease. Consequently, devices and methodologies that employ relatively elevated temperatures (i.e., "above normal") as a test criterion for infection are routinely used as a default approach for prescreening diagnostics. In a recent study, a COVID-19 screening project to check for individuals having high fever temperatures and COVID-like symptoms at U.S. airports caught fewer than 15 cases out of 675,000 travelers.

Typically, the thermal imaging cameras and devices measure maximal facial temperatures of subjects to generate and display a rainbow-colored thermal profile of the subject that leads to a pass/fail outcome. A reading above 101-F (38.5 C) from a single test is recognized as a trigger to provide alerts to the testing agent and/or the test subject. When the trigger or alert occurs, certain actions and/or limitations may be required of, or imposed upon, the test subject. For example, the test subject may receive a recommendation to see a health care profession for further diagnostic testing and evaluation. The test subject may be restricted or delayed from entering a facility such as a workplace, library, school, university, hospital, or nursing home. In addition, test subjects with elevated facial temperatures may even be required to strictly comply with government mandated requirements such as limitations on travel, medical confinement, isolation, and/or self-confinement for a predefined period.

Both fixed location and portable IR thermal sensing devices are commercially available and have been placed into widespread use in facilities such as government and public buildings, universities, hospitals, airports, and the like. Some devices can establish facial-region temperatures of large groups, where individuals exhibiting "abnormally" elevated temperatures can be pin pointed and segregated from the group as needed to allow for more-relevant diagnoses to be performed. The Center for Disease Control (CDC) warns that even when these devices are used properly and preferably on individual subjects, temperature assessments may have limited impact on reducing the spread of infectious disease such as COVID-19. CDC studies suggest that simple temperature measurements alone may miss more than half of infected people. Thus, these IR thermal sensing devices that are used to screen for illnesses fall extremely short of what is urgently required to manage the COVID-19 epidemic and the like. The present IR sensing devices and related testing methodologies may be described as single parameter tests with extreme limitations.

While the presently known IR sensing devices are convenient to use, the results they produce, unfortunately, do not correlate with illness. This is particularly true in cases of those individuals who are asymptomatic carriers—those persons who infected with a pathogen, but display no signs or outward symptoms. Such individuals may carry and transmit the virus, but exhibit no observable symptoms. These individuals usually require invasive, clinical level evaluation to confirm presence of a virus. Clearly, the single-parameter temperature-measuring devices fall far short of what is required to assure diagnostic accuracy and high confidence results. Further, the fixed-location, temperature-measuring test stations that are in common use are easy to defeat or circumvent entirely.

There is an ongoing need for devices and methods that have expanded and foolproof capabilities to measure, analyze, and report on a large number of symptoms and pre-symptoms for reliable correlation with COVID or other virus-based illnesses. These devices and methods also need to capitalize upon a plurality of symptomatic, pre-symptomatic, and asymptomatic biometric parameters to improve diagnostic accuracy during the prescreening and other diagnostic phases of illness detection and remediation. The devices and methods of the present invention overcome at least one of the disadvantages associated with conventional devices and avoids or ameliorates at least some of the disadvantages of conventional devices/methods.

SUMMARY

In one aspect, the invention provides a biometric imaging and biotelemetry system that includes at least one data acquisition apparatus, a preprocessor, a central processor, and a controller unit. The at least one data acquisition apparatus captures biometric data. The preprocessor has electrical communication with the data acquisition apparatus. The preprocessor analyzes the biometric data by performing at least one of calculating, comparing, and contrasting the biometric data in relation to at least one of programmed specifications, norms, and protocols. The central processor has electrical communication with the preprocessor. The central processor processes the analyzed biometric data from the preprocessor with at least one of high-performance computing, advanced mathematical algorithms, and block-chain systems. The central processor determines a subject-specific profile. The controller unit has electrical communication with the central processor, the preprocessor, and the data acquisition apparatus. The controller unit to program and modify and to direct and control data flow, analysis, and reporting of the central processor, the preprocessor, and the data acquisition apparatus. The controller unit externally transmits the subject-specific profile.

In another aspect, the invention provides a biometric imaging and biotelemetry method that includes capturing biometric data, analyzing the biometric data, performing at least one of calculating, comparing, and contrasting the biometric data in relation to at least one of programmed specifications, norms, and protocols, processing analyzed biometric data with at least one of high-performance computing, advanced mathematical algorithms, and block-chain systems, determining a subject-specific profile, and externally transmitting the subject-specific profile.

In another aspect, the invention provides a biometric imaging system that is configured to acquire and capture a visible-light digital image of at least a portion of an individual, and deconstruct the captured digital image into individual and identifiable subregions where each subregion may be configured to represent at least one microscopic area of the individual that equates to between 1 and 1,000,000 square microns.

In another aspect, the invention provides a biometric imaging system that is configured to acquire and capture a thermal digital image of at least a portion of an individual, and decompose the captured digital image into individual and identifiable subregions where each subregion may be configured to represent at least one microscopic area of the individual that equates to between 1 and 1,000,000 square microns.

In another aspect, the invention provides a biometric imaging system that is configured to acquire and capture a digital image of at least a portion of an individual, by use of at least a portion of the ultraviolet region of the electromagnetic spectrum, and upon image acquisition to decompose the digital image into individual and identifiable subregions where each subregion may be configured to represent at least one microscopic area of the individual that equates to between 1 and 1,000,000 square microns.

In another aspect, the invention provides a biometric imaging system that is configured to acquire a combined visible-light and thermal digital image of at least a portion of an individual, and decompose the combined digital image into individual and identifiable subregions where each subregion may be configured to represent at least one microscopic area of the individual that equates to between 1 and 1,000,000 square microns.

In another aspect, the invention provides a biometric imaging system that is configured to acquire a digital image of an individual where the image is formed by an image capture process employing any selected region or regions of the electromagnetic spectrum, and upon capture of said image to decompose the digital image into individual and identifiable subregions where each subregion may be configured to represent at least one microscopic area of the individual that equates to between 1 and 1,000,000 square microns.

In another aspect, the invention provides a biometric imaging system that includes at least one preprocessor subsystem configured to receive at least one digital data stream which may arrive at the preprocessor in the form of an image-configured data format, where the preprocessor serves to receive and transpose the incoming data stream into a format suitable for mathematical digital processing, and where the transposed data suitable for mathematical digital processing may be defined as digitized biomarker data.

In another aspect, the invention provides a biometric imaging system that includes at least one central processing system configured to receive at least one data stream in the format of one of a preprocessor transposed data and an image-formatted data, where the central processor has at least one software-based program with at least one mathematic algorithm that provides the central processor with a capability to at least one of analyze the data stream, select and extract data from the data stream for use in performance of at least one mathematical calculation, draw intelligent conclusions from the calculation results, generate detailed and summary reports, and direct subsequent data and report outputs to at least one pathway interconnecting the central processor with encoding and decoding protocols for user interface devices and accessories, and for local or remote storage.

In another aspect, the invention provides a biometric imaging system that is configured to acquire a digital image of an individual where the image is formed by an image capture process employing any selected region of the electromagnetic spectrum, where one of a camera and a sensor, upon capture of said image, decomposes the digital image into individual and identifiable regions where each region may have an area equal to between 1 and 1,000,000 square microns, and where each region is related to a biologically related parameter referred to as a biomarker.

In another aspect, the invention provides a biometric imaging apparatus that includes a set of at least two, high-performance digital camera sub-systems, at least one Specialized Synthetic Intelligence (SSI) interface, at least one application specific integrated circuit (ASIC), at least one custom Block-Chain protocol, an interfacing operating system (OS) with optional graphical user interface (GUI), an integration protocol for use on existing platforms, an optimization function for at least one of Data Structure, Big-0 notation, Deep-Learning, and Machine Vision, a set of interconnecting paths, where the interconnecting paths are at least one of wires, cables, fiber optics, and networking circuits, and at least one digital display unit.

In another aspect, the invention provides a multifunctional biometric imaging apparatus that includes a set of at least two, high-performance digital camera sub-systems, at least one Specialized Synthetic Intelligence (SSI) processor, at least one application specific integrated circuit (ASIC), at least one data node, at least one custom Block-Chain protocol, a set of interconnecting paths, where the interconnecting paths are at least one of wires, cables, fiber optics, and networking circuits, and at least one digital display unit.

In another aspect, the invention provides a biometric imaging method that includes acquiring image data from an individual by use of at least one data acquisition apparatus subsystem having at least one of a high-resolution digital camera and a sensor, transmitting image data in the form of a digitized data stream to a preprocessor subsystem, where the preprocessor serves to receive the image-formatted data stream and employ at least one mathematical algorithm configured to interact with a data achieve, and constructing projections and preliminary conclusions. The preprocessor is enabled to assign actionable tasks relating to incoming data volume and quality, establish how much of this data stream is to be achieved, initiate and direct the achieving operation, determine subsequent operations and transmit at least one of an original data stream and a reformatted data stream along with executable commands to the subsequent operation, assign unique biomarker identity to each data element within the selected set that will eventually be employed in pre- and post-processing operations, and determine if the at least a portion of incoming data may fall under that category of information including an individual's medical records and history, which are protected under the Health Insurance Portability and Accountability Act (HIPAA).

Other systems, methods, features and advantages of the invention will be, or will become, apparent to one with skill in the art upon examination of the following figures and detailed description. It is intended that all such additional systems, methods, features, and advantages be included within this description, be within the scope of the invention, and be protected by the claims that follow. The scope of the present invention is defined solely by the appended claims and is not affected by the statements within this summary.

BRIEF DESCRIPTION OF THE FIGURES

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 13 represents a tabulation of factors that may serve to obscure and complicate an image-based medical diagnosis.

FIG. 15 represents a tabulation of factors that may be acquired in an initial form of image data then may undergo transformation and analytic processing during progression(s) through various subsystems of a biometric imaging and biotelemetry system.

FIG. 16 represents an illustration of an example display of medical diagnoses delivered by a digital display member to a system user.

FIG. 17 represents a tabulation of a subset of parameters as described in FIG. 15 that have been selected for making the electronically composite images of the exemplary medical diagnosis shown in FIG. 16.

DETAILED DESCRIPTION

Figure 1:
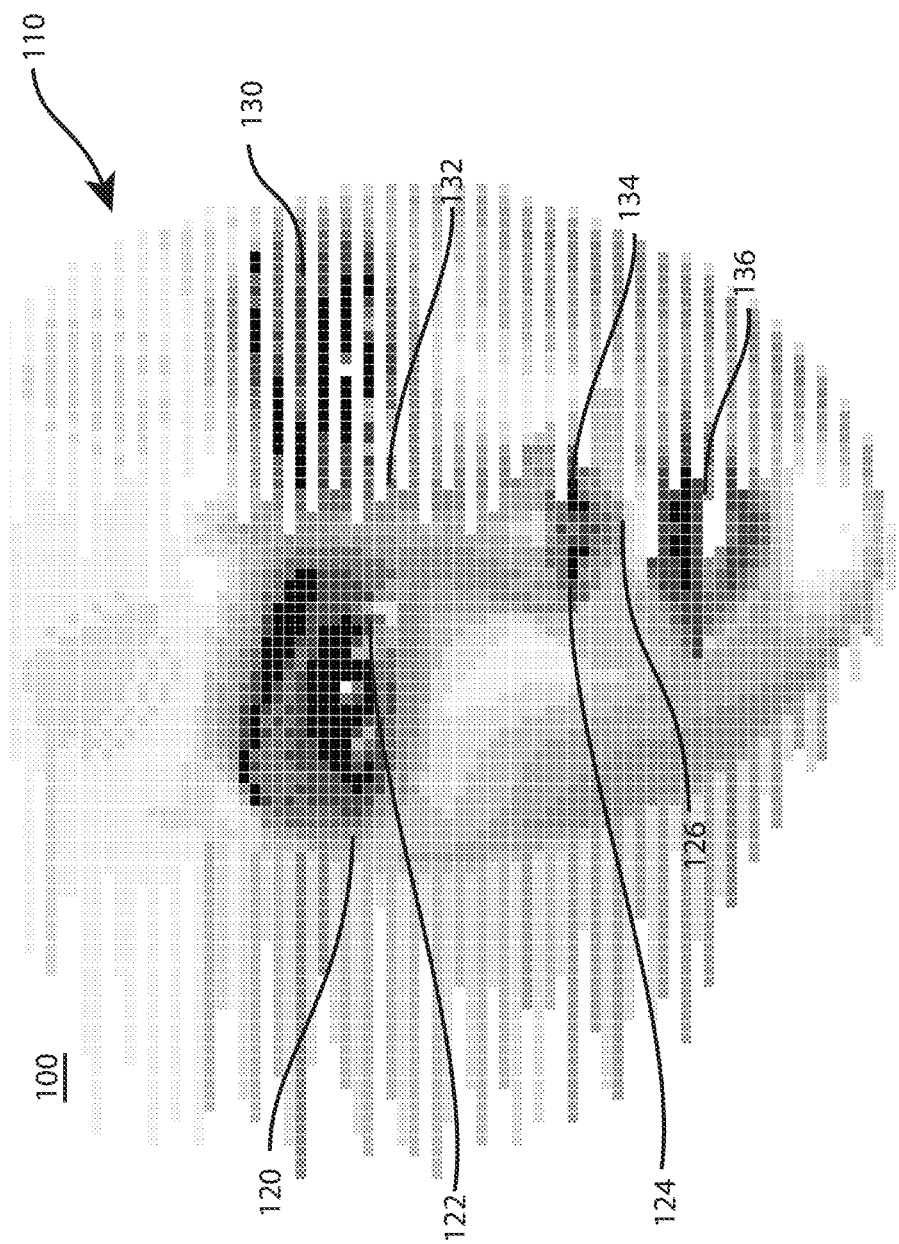
FIG. 1 represents a macroscopic facial region of a test subject that is spatially decomposed into microscopic pixel subregions.

A biometric imaging and biotelemetry (BIB) system has been developed that may be configured to capture, analyze, and process qualitative and quantitative biomarker data acquired from the process of imaging of individuals. The BIB system is an intelligent multifunctional biometric imaging system that can rapidly measure facial and other body temperatures of a human test subject, along with a plurality of other biometric parameters that may be compiled into a subject-specific health profile which, in turn, may provide insights into the wellness or illness of the individual. The BIB system uses a multiplicity of biometric data that may be remotely collected and intelligently mined in such a manner to increase the accuracy of medical diagnoses. The BIB system avoids using the insufficient quantities of such data that limits the reliability of medical diagnoses from conventional devices and methods for diseases such as COVID-19. The BIB system captures vast amounts of biometric data by appropriately configured, multispectral, high resolution digital cameras and sensors. This data is then interconnected to a series of data processing units that employ custom algorithms, artificial intelligence, and self-learning/deep learning to analyze and process data and render decisions and manage actions via complex analytical methodologies. The BIB system provides essentially instantaneous analyses that give real-time insights into the wellness or illness of a test subject.

In the BIB system, one or more multifunctional, digital display units are configured to provide user-selectable audio, image, and/or text output-options. The digital display units may be configured into a variety of report formats that include such options as direct real-time information displays, printable documents, transmittable data files, magnetic, optical, microchip, or other stored data, audial and/or visual commands and/or instructions, combinations thereof and the like. The BIB system may be designed to function as a rapid, effective, and non-invasive means to prescreen for and help diagnose COVID-19 and other virus borne illnesses. The BIB system is easily customized to not only meet the requirements of a wide variety of medical and medical research applications relating to human, veterinary, and vegetation arenas, but to many others as well including criminology and law enforcement, architectural and structural inspection, intelligent machine vision and failure diagnostics, and the like.

The BIB system may use Artificial Intelligence (AI) and compact super computers to collect, analyze, and process vast amounts of data as well as to generate, refine, simulate, prepare and test recommendations and/or conclusions from a single cause and effect event. Further, the BIB system may use proprietary Specialized Synthetic Intelligence (SSI) processors and highly functional SSI-based software to create and deploy specific-purpose, advanced algorithms, data networks, and interfaces that enable processing, analyses, and transference of extremely large amounts of data and information in extremely short periods of time.

The BIB system also may use specific modes of integration of SSI processors with Block-Chain encryption. The BIB system thus configured would provide a vehicle to create SSI based program elements, referred to as "seeds". These SSI based program elements would enable immediate data deployment, archival, transmission, and/or security-encoding/decoding functionalities that enable massive amounts of data and information to be securely transmitted and distributed at an extremely high rate. For example, data transmission rates of at least 500,000 data events per second could be used.

The BIB system may use high-performance digital cameras, camera sub-systems and sensors that may be coupled to at least one, and preferably at least two, advanced Specialized Synthetic Intelligence (SSI) processors. When the BIB system is configured with Block-Chain encryption protocols, the BIB system may serve to acquire a plethora of facial data or external biomarkers on either single or multiple subjects. Once the facial data or external biomarkers are acquired, a complex algorithm within a central processor may be employed to direct intelligent screening, archival, evaluation, and to manage a set of analytical and transmission operations. The central processor may have at least one other complex algorithm. The one or more complex algorithms provide results that, not only detect and display the temperature profiles of the test subject, but also collects, records, analyzes, manages and displays a plurality of other symptom-related information and attributes.

The BIB system may deploy Block-Chain encryption protocols to enable interconnection and interaction with the "cloud" and to employ "cloud computing" via a large number of data centers available to users in real time over the Internet. This network of remote servers is specifically hosted on the internet to serve to store, manage, and process data, and thus may serve to off-burden a local system's server or related personal computer(s) from routine or other tasks that may be remotely accomplished. Importantly, the cloud and cloud computing allow the BIB system to transmit, receive, and distribute encrypted data and programming functionalities to preselected remote locations apart from the main processor of the BIB system.

The BIB system is described in detail with reference to the accompanying drawings. Numerous specific details are set forth in order to provide a thorough understanding of the different aspects. These and other aspects may be practiced without some or all of these specific details. In addition, the methods or related processes may have other features and operations that are omitted from the figures in order to not obscure the salient aspects. Likewise, the devices or related apparatuses may have other components and elements that are omitted from the figures in order not to obscure the salient aspects of the disclosure.

Figure 4:
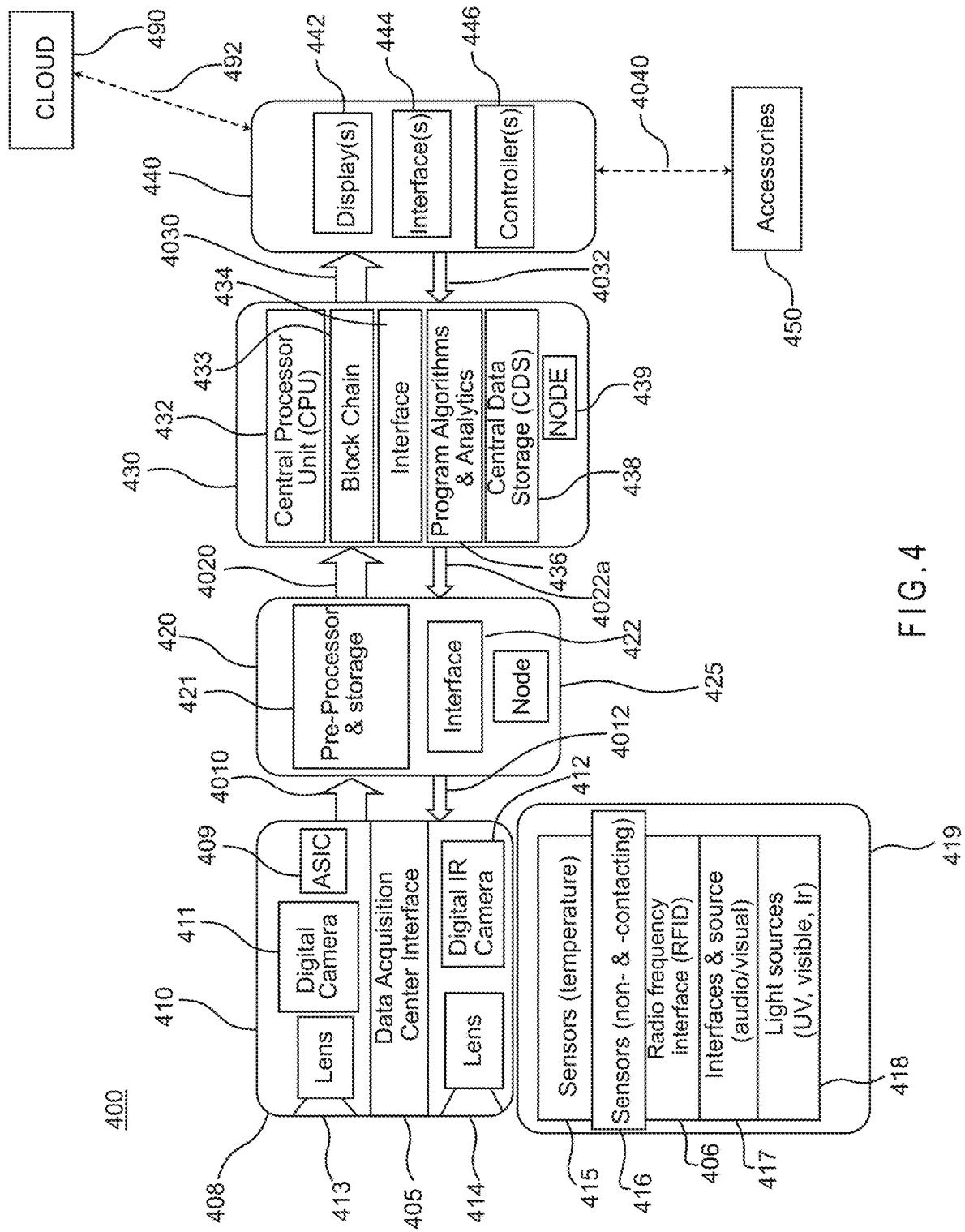
FIG. 4 represents a block diagram of a biometric imaging and biotelemetry system.

FIG. 4 represents a block diagram of a biometric imaging and biotelemetry (BIB) system 400, which is an intelligent and multifunctional biometric imaging apparatus configured to function as a medical diagnostic apparatus. The BIB system 400 includes a set of at least two, high-performance digital camera sub-systems 411 and 412 that may be enveloped within a suitable housing such as a Data Acquisition Apparatus (DAA) 410. The digital camera subsystems 411 and 412 are electrically connected to or have electrical communication with at least one Specialized Synthetic Intelligence (SSI) preprocessor 420, employing an advanced high-performance computing (HPC) and storage apparatus 421 and data interface 422. The SSI preprocessor 420 is electrically connected to or has electrical communication with at least one Specialized Synthetic Intelligence (SSI) central processor 430, employing an advanced high-performance computing (HPC) system 432. At least one application specific integrated circuit (ASIC) 409 is disposed within the DAA 410 and electrically connected to the digital camera sub-system 411. The BIB system 400 also includes at least one data node 425 and 439, where the data node 425 is operatively disposed in the SSI preprocessor 420, and where the data node 439 is operatively disposed in the SSI central processor 430. At least one custom Block-Chain protocol 433 is included with the SSI central processor 430. At least one digital display unit 442 is electrically connected to or has electrical communication with the SSI central processor.

Optionally, the DDA 410 is electrically connected to or is in electrical communication with a sensor subsystem 419, which includes at least one of a sensor 415, a detector 416, an audio source or receiver 417, and a light source 418 that is configured to function within at least in one part of the electromagnetic energy spectrum such as a narrow spectral region and an ultraviolet (UV) region. Optionally, at least one interconnecting, encoded linkage 492 interconnects the BIB system 400 with the "cloud" and related "cloud computing" 490. As a further option, at least one external system interface accessory 450 or electromechanical device is operatively connected to the at least one digital display 442. The BIB system may include one or more of a set of interconnecting wires, cables, fiber optics, radio frequency (Rf) receiver(s), RF transceivers, peripheral component interconnect (PCI), network cards, combinations, or the like which are not shown.

The BIB system 400 may be configured alternatively as four modules or "subsystems"—a Data Acquisition Apparatus (DAA) 410, a Synthetic Intelligence (SSI) preprocessor 420, a Central Processing Unit (CPU) 430, and a System Controller Unit (SCU) 440—each subsystem having electrical communication with at least one other subsystem. "Electrical communication" includes at least one of electrically connected and non-electrically connected: where electrically connected means components communicate with each other by means of a conducting path such as through a wire, a cable, other conductors, circuitry, combinations, and the like; and non-electrically connected means components communicate with each other with or without a conducting path such as with radio signals, lasers, cellular or other telephones, WIFI (wireless fidelity) or other wireless network protocols, satellites, combinations, and the like. Components with electrical communication may be both electrically connected and non-electrically connected; for example, components may be electrically connected to supply electrical power and non-electrically connected to transfer data and operating signals. "Electrical communication" also includes when components are operatively connected to perform a particular function.

The Data Acquisition Apparatus (DAA) 410 serves to sense and acquire biometric data from a test subject. Preferably, the facial image of a human is the test subject. However, other human images may be used. FIG. 1 represents the facial image of a test subject 110.

The SSI preprocessor 420 consists of a Data Preprocessing Apparatus (DPA) 421 that serves to receive the biometric data from the DAA 410 via an appropriately configured interface 405 and interconnection 4010 and then via use of a specific DPA interface integrated together with a specific, intelligent and self-learning processor 421 along with appropriately configured algorithms (not shown) functions to calculate, compare, and contrast the incoming data against preprogrammed specifications, norms, and protocols that may be stored locally within the preprocessor 421. Within the DPA 421 is a provision to store selected data as prescribed by one, or more DPA algorithms. Then, at the same time, the DPA 421 serves to segregate portions of the incoming data from otherwise routine, secondary analytical processing when each data element has been determined to fall short of meeting preestablished specifications. The subset of segregated data may be appropriately formatted and passed directly on via at least one data interface 422 and interconnection 4020 and 4030 to a suitable display 442 or other data output accessory 450.

The Central Processing Unit (CPU) 430 receives the remaining data subset from the DPA 420 through a specially configured interface 434. Within the CPU 430, the incoming data is analyzed and processed by use of a Specialized Synthetic Intelligence (SSI) 432 processor. The CPU 430 is configured with advanced mathematical algorithms 436, executable instructions, at least one central data storage module 438 and an inter-module interface 434, at least one neural networking node 439 and various inter-subsystem interconnections 4020, 4022, 4030, and 4032.

The System Controller Unit (SCU) 440 receives the processed data as a subject-specific profile in the form of parameters, groupings of parameters, data matrices, one or more digitized data streams, mathematical functions, analytical conclusions, graphic relationships, operational instructions, combinations, and the like. The processed data may take on the form of any suitable formatting and may be encoded for optional external transmission 492 to the cloud 490 or the like. The SCU 440 is configured to perform the following functions: (1) interface and interact with each of the subsystems and accessories; (2) enable programming and modifications to programs including downloading of externally generated programs to any designated subsystem; and (3) serve to direct and control the flow of data throughout the system. The BIB system 400 may also include multiple data pathways 4010, 4020, 4030, 4012, 4022, 4032, 4040, and 492 configured to communicate and share appropriately configured data and commands between and amongst the system subsystems.

The BIB system 400 may have one or more other scanners or sensors. The BIB system 400 may have at least one non-contacting iris scanner. The BIB system 400 may have at least one contact sensor 416 configured to acquire biometric data via direct, albeit non-invasive, contact with the test subject. This at least one sensor 416 enables the BIB system 400 to acquire, analyze, record, and integrate supplemental biometric data into a medical diagnosis as a means to help improve the accuracy of the resultant medical diagnosis. The at least one contact sensor 416 may comprise an identity badge reader, a credit card reader, a fingerprint reader, an oxygen sensor, a sphygmomanometer such as a blood pressure cuff, an ophthalmoscope, combinations, or the like.

The BIB system 400 may have at least one sensor (not shown) configured to acquire data, such as identification data related to an individual, via a device such as an employee identification badge, a credit card, a health or other insurance card, or a health-related file. The sensor may be configured to operate as a magnetic reader, a reflected light reader, a laser light reader, a bar chart reader, a glyph reader, combinations, or the like.

The BIB system 400 may have at least one sound emitter or receiver 417, at least one light emitting source 418, combinations, or the like.

The BIB system 400 may have a sensor subsystem 419, which may include at least one interface 406 which may be a RFID configured interface, at least one sensor 415 and 416, and at least one source 418 integrated and contained within a suitable enclosure and located either integrated with, adjacent, adjoining, or remotely located from the camera module 408.

The BIB system 400 may have a Data Acquisition Apparatus (DAA) 410 that serves to sense and acquire biometric data from a test subject 110. The DAA 410 is comprised of at least one camera module 408 configured to house, encase, protect from damage, and enable positioning and mounting of at least one high resolution digital camera 411, at least one lens 413, at least one application specific integrated circuit (ASIC) device 409, and at least one data interface 405. The camera 411, the lens 413, the ASIC device 409, and the interface 405 may optionally be integrated into a self-contained assembly. The camera module 408 may also be configured to contain, encase, and protect from damage at least one thermal image sensor 412, related lens 414 and ASIC device 409.

Figure 8:
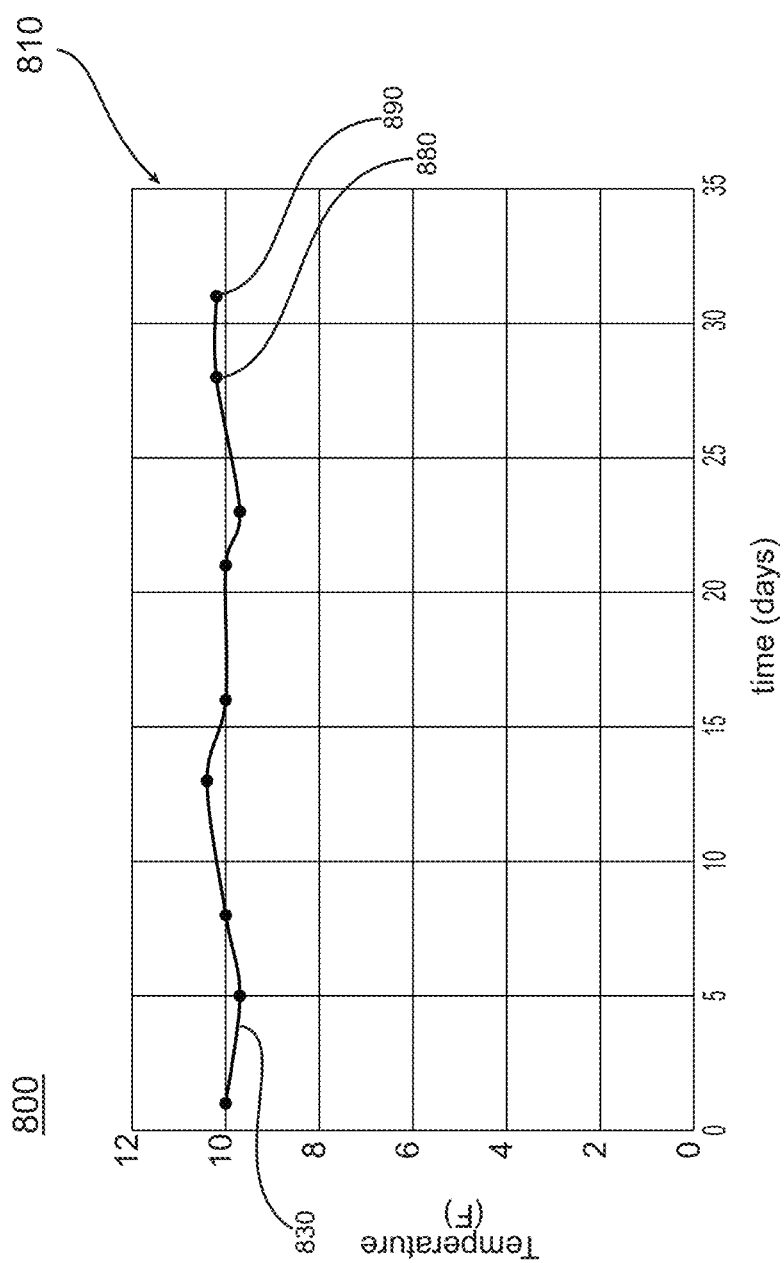
FIG. 8 represents a graphic illustration of time-based, differential temperatures of a hypothetical subject.

The DAA 410 preferably uses imaging cameras and IR sensors having high pixel counts, ultra-high resolution (preferably 120 MP or more), and high operational and data transfer rates with faster readout speeds and with lower noise ratios preferably at 50 frames per second (fps) or higher. Suitable cameras and sensors are the Canon 3U5MGXSBA and the Canon 120MXS CMOS sensor which are manufactured and sold by Canon US. The Golden Eye G-034 TEC1 produced by Allied Vision is another example as to the image sensors. These and similar units are deemed to function suitably as components of the Data Acquisition Apparatus 410, which may have at least one camera member 411, at least one sensor member 412, and at least one aperture 413 and 414. Further sensing technologies are emerging that may also be suitable for deployment within the DAA 410. An example of a functional enhancement to a camera unit and ASIC component is a high precision temperature sensing member that is integrated within the camera unit that may serve to monitor intra-device temperatures and ambient temperatures, to reduce overall size of the camera module, and to increase data transmission efficiency. The combination of thermal data may be employed to determine thermal differentials 830 and 840 as shown in FIG. 8 and in FIG. 9.

The BIB system 400 may be deployed with other components such as PCIe add on cards such as, but not limited to, the PCI Express Host Adapter card (not shown) sold by Allied Visio. The ASIC device 409 can include, but is not limited to, Nvidia Jetson platform with breakout board attachments including Jetson Nano, Jetson Xavier, and the likes. The ASIC device 409 also can include, but not limited to, Nvidia GPU modules including RTX series, Quadro, DPU, and Tesla modules. In order for the BIB system 400 to function at capacity, the pre-possessor GPU 421 and the Central Processor 430 must have, at a minimum, the present capabilities presently provided by commercially available models PCI express 4.0 and 3.0. The CPU 430 should have, but is not limited to, larger and scalable capabilities, multi-thread capabilities, and optional voltage increase/decrease for single node use per CPU. Example CPU's are, but not limited to, AMD CPU's (preferably, AMD thread ripper series), Intel scalable Xenon processors, and the likes.

In order for the BIB system 400 to function at capacity, it is highly desirable to maximize the bandwidth of data transfer within and amongst each subsystem system. The interconnection devices 4010, 4020, 4030, 492, 4012, 4022a, 4032, 4040 may be manufactured and sold by Cisco, Mellanox, and Nvidia, which have been found to provide sufficient bandwidth (e.g., in the range of 1 byte to 1000 petabytes) to acceptably serve as inter-subsystem and external network linkage functions. Alternatives to achieve connection and/or interconnection functionality may be done via a direct PCI express connection, Wi-Fi enabled, Bluetooth, network circuits, fiber optics, ethernet cat 6A or above, cable, or combinations or the like.

The BIB system 400 may utilize a vast assortment of interconnection cables including commercially available products referred to as LinkX Ethernet DACs and AOCs being 1G-100G's. Similarly, a vast assortment of high definition (preferably having a pixel density of at least 80 pixels per inch) and high frame refresh rate (preferably a refresh rate of at least 60 Hz) may be utilized as display units including commercially available products such as those manufactured and sold by Acer, Alienware, Samsung, and Apple.

The DAA 410 may be configured with a light source 418 having the capability to emit white or broad-spectrum light, or alternatively, to emit light having at least one preselected wavelength or range of wavelengths. The light may be unpolarized or polarized dependent upon the specific requirements of the diagnosis under assessment and/or an instruction set issued by the BIB system 400. In addition, the light source may be configured to emit various intensities of at least one designated wavelength or of a range of various and perhaps blended wavelengths to create a composite. The intensity of constituents of the composite may be constant or variable. Further, the light intensity may be constant over a designated period of time or variable as determined via designations of selectable light characteristics (e.g., wavelength(s), mix of wavelengths, intensities, and time intervals), which may be established by a suitably constructed data exchange between and amongst the DAA 410, the SSI preprocessor 420, and the CPU 430.

Emitted light from the light source 418 may be used to enhance and/or expand the diagnostic capabilities of the BIB system 400. The light source may be an appropriately configured multi-spectrum light emitting source having a blend of wavelengths and intensities that are modified to help reveal what otherwise may be invisible or nearly-invisible biomarkers. For example, a multispectral light source having alternating high levels of the blue and red spectral regions may be used to illuminate the neck region of a test subject (for example, see 263 in FIG. 2). Under these conditions, the carotid artery becomes quite visible when illuminated by a properly configured light source even if carotid artery is located below the surface layer of the neck. Subsequent imaging over a period of about a month reveals that a statistically significant enlargement in this artery has been observed and that the temporally-based enlargement may be correlated with the onset of hypertension in the subject patient. A similar finding has been observed when a major artery in the forearm region of a patient, who has been imaged and analyzed under similar conditions, and whereafter a clinical physician validated the pre-diagnosis and prescribed a plan of treatment.

In a further example, upon processing an initial stream of image data and conducting preliminary analyses on a test subject, an initial determination is reached by the AI processors that a particular group of ailments such as rosacea, COVID-19, flu, cold, or other suspected ailment may be distinguished by one or more facial colorimetric indicators, which may be present and employed as a biomarker(s). The at least one of the camera units 411 and 412 of the DAA 410 has served to acquire at least one facial image representing the entire colorimetric spectrum. The full-color spectrum data is delivered from the camera module(s) 411 and 412 to the Data Acquisition Center's interface 405, which serves to direct the image data stream to the SSI preprocessor 420. The SSI preprocessor validates the incoming data stream 4010 and then encodes the colorimetric image data into at least one computer processable data format, which may be referred to as machine augmented data. The SSI preprocessor 420 directs a selected portion of the data stream 4020 to the CPU 430 and working in concert perform a series of AI-enabled analyses that then establish a preliminary diagnosis. To arrive at the preliminary diagnosis, AI and algorithmic enabled comparatives are conducted by use of at least one of symptom-characteristics, medical records, case records, real-time updates, combinations, or the like that have been internally achieved as a library in the Central Data Storage (CDS) unit 438, and/or optionally provided via interconnection(s) with the internet and/or the cloud 490. The processors' comparisons of color-specific biomarkers result in an issuance of a stream of commands that are conveyed 4012, 4022 to the light source unit 418, which serves to configure the spectral and temporal composition and emit a specifically configured light sequence to illuminate the test subject with at least one image coloring enhancement that may be employed in a follow-on image acquisition process and re-analysis of the color-enhanced image. Such color enhancement may be particularly useful when the BIB system 400 has insufficient (or confusing) data to generate a clear diagnostic conclusion. An example may be the case where the initial facial imaging of a test subject records a somewhat elevated maximal temperature (Tmax) along with a number of reddish appearing regions. The regions are observed along both edges of the nose and within the eyes. The regions appearing as reddening of the white portion of both eyes believed to be symptomatic of blood vessels on the surface of the eyes that are expanded (i.e., dilated) due to a form of infection and not due to an artifact of the imaging process. A fresh set of images is acquired by the DAA 410 under various lighting conditions configured to emit certain light wavelengths for designated time periods. A lighting sequence, for example may comprise at least one of a narrow blue spectrum component and at least one red spectrum component projected individually onto the subject for a similar brief period (e.g., 100 ms). The red-light component may serve to obscure, darken, or black-out the reddish regions while the blue-light component may serve to highlight the reddened regions and thus enable a better definition of the colored regions. The precise areas and color intensity of the reddened regions may thus be easier to precisely quantify and enter as such into the individual's profile for further reference. If upon subsequent evaluation after passage of time (e.g., 24 hours as in the case where an employee receives a routine daily evaluation prior to permitted entry into a workplace), changes to the reddened biomarkers may be observed and employed to aide in a medical diagnosis. Depending upon the nature, location, intensity of the changes, the system may display advisory messages to the individual, to the system administrator, and/or clinician, where upon appropriate action(s) may be taken to follow-up to the advisory message.

In the present example, where a slightly elevated maximal temperature (Tmax) and reddening of nose and eye regions have been observed, the light source may be employed to illuminate the test subject using a sequence of unpolarized light followed by polarized light. A comparison of the reflected images under these specific illumination conditions may better define a subregion immediately below the nose wherein a liquid-like substance may be observed and associated with a nasal discharge. The system may analyze this combination of quantified biomarker parameters (see 1570 in FIG. 15) consisting of Tmax, CRE, CLE, CNL, CNR, CDEL, CDER, CDNL, and CDNR along with the nasal discharge observation, and thus generate and display a diagnosis 1600 as represented in FIG. 16. FIG. 16 represents an illustration of an example display 1690 of medical diagnoses delivered by a digital display member to a system user and thereby providing the user with high confidence insights into the wellness or types of illness that may be impacting upon a test subject. Given the enormity of data generated in this particular transaction, the BIB system may be configured with advanced algorithms that provide the capabilities to further mine the data and project that these particular symptoms better align with those of a particular ailment such as a cold as opposed to other ailments (see the suspected group 1691 in FIG. 16).

The BIB system may be incorporated solely in two modules. The first module is a remotely locatable DAA subsystem 410 that is wirelessly interconnected to a highly integrated, multifunctional processor subsystem. The processor subsystem may be configured to house the entirety of constituent components previously described (i.e., 420, 430, 440, 421, 422, 425, 432, 433, 434, 436, 438, 439, 442, 444, and 446), and in so doing will yield a more compact unit. A suitable processor module to serve for the combined processor functions as well as the as a housing unit is the Dell EMC server 7525 manufactured and sold by Dell Technologies or the like. This product has been shown to have the required capabilities for housing all processors, preprocessors, algorithms, storage, nodes, controllers, displays, and sensors, or any combination.

The BIB system 400 may be a multifunctional biometric imaging apparatus having at least one sound sensor, a sound transmitter, a light sensor, or combinations.

The BIB system 400 may be a multifunctional biometric imaging apparatus having at least one radio frequency (RF) interface 406 configured to receive and optionally to transmit and/or exchange RF data and/or information with a suitably configured external device such as a Radio Frequency Identification Device (RFID), which is not shown. The RFID device, also referred to as a RFID tag or RFID badge, may serve to identify an individual to the system, to a system administrator, or combinations.

The BIB system 400 may be a multifunctional biometric imaging apparatus having at least one temperature sensing device 415 that is configured to measure environmental temperature(s) within the ambient environment where at least one of the system components resides and operates. The at least one temperature sensing device 415 may be a digital thermometer, a thermistor, a thermocouple, and the like.

The BIB system 400 may be a multifunctional biometric imaging apparatus having at least one Data Acquisition Apparatus 410 with at least one camera module 408, at least one high resolution, visible light camera 411 configured with a suitable lens 413 and optional filter, at least one infrared (IR) thermal sensing camera 412, with lens and optional filter 414, at least one custom Application Specific Integrated Circuit (ASIC) 409, an interface 405, and at least one interconnecting data pathway 4010 and 4012 consisting of fiber optics, ethernet link, combinations, or the likes.

FIG. 1 represents a macroscopic facial image 100 of a test subject 110. Selected regions representing the left half of the face appear with pixel designated subregions 120, 122, 124, and 126, where the test subject's facial characteristics are easily recognizable. Within the test subject image 110 are similar, albeit opposing, subregions that have been more fully transposed to illustrate discrete pixel-configured subregions 130, 132, 134, 136 that may be processed by the BIB system 400 in the format of digitized image data.

Figure 2:
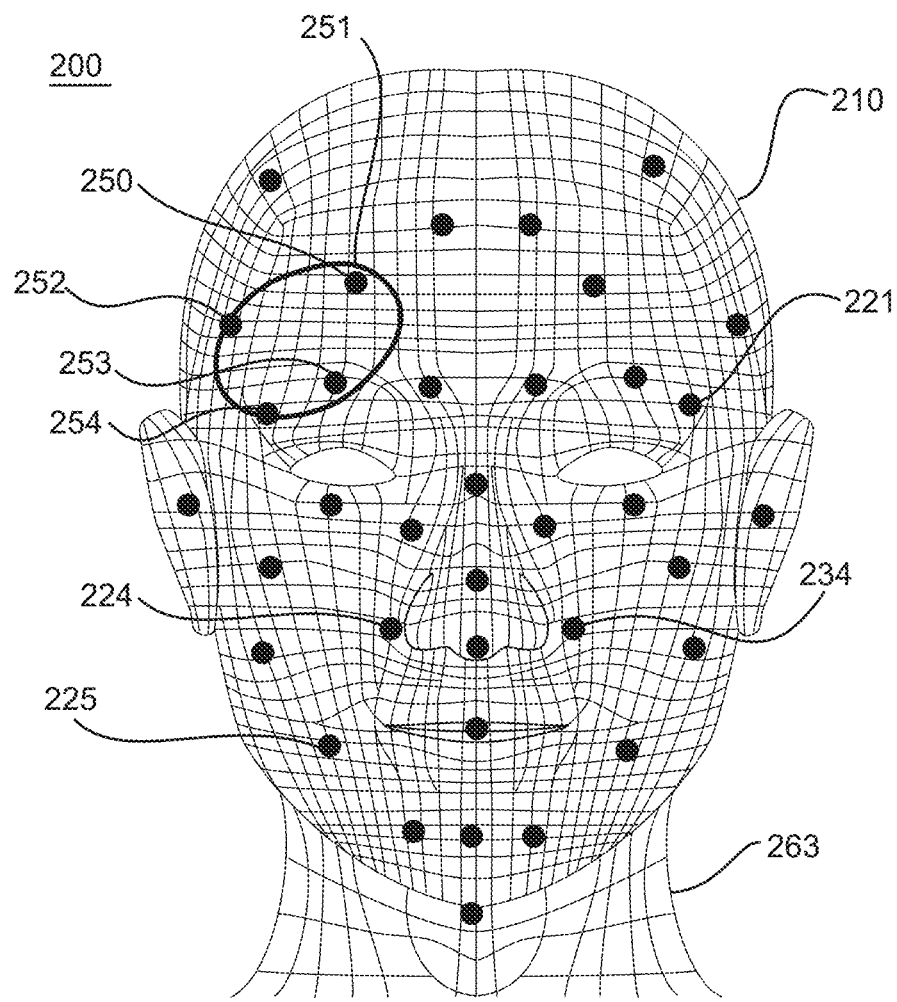
FIG. 2 represents a portrayal of a head region having spatially separated spot-size microregions.

Portions of the facial region 110 of FIG. 1 are illustrative of an image captured by the camera module 410 and prepared for processing by the preprocessor subsystem 420 as described in relation to FIG. 4. The subregions 120, 122, 124, 126 as well as the opposing selected group of subregions 130, 132, 134, 136 may be resolved entirely into pixels; that, upon so doing, may be formatted into a surrogate head region 200 comprising spatially separated spot-size microregions as represented in FIG. 2 and made available in that form for further processing and analysis.

The average human head is approximately 6 to 7 inches wide (about 150 mm to 200 mm) and approximately 8 to 9 inches high (about 200 to 230 mm). The average circumference of a face is approximately 21 to 23 inches which equates to areas of approximately 30,000 to 40,000 square millimeters. Males generally have a slightly larger head than females, while the heads of children may be significantly smaller. Given that a typical pixel size may be approximately 8 $\mu m^2$ to 15 $\mu m^2$ (square microns or micrometers) in size, it is easily recognized that a typical facial region, even those of children, may be easily partitioned into many thousand, hundreds of thousands, and even many millions of pixel-sized elements. Each of these elements may serve as a biomarker. As high-resolution imaging technology continues to evolve, it is not unreasonable to expect that digital image-related pixel-sizes in the range of about 0.5 $\mu m^2$ to 5 $\mu m^2$ (square microns or micrometers), or smaller may be forthcoming. Given such developments, the capability may emerge to enable partitioning of facial images into billions, or even many more, pixels via what may be referred to as ultra-high-resolution digital imaging methods. Although the descriptions of the BIB system 400 are framed with reference to presently known and/or available equipment and technologies, it is intended that the present invention not be limited to, nor constrained by, the present state of imaging art.

Each pixel regardless of size or shape, or optionally small domains of associated pixels, may be grouped in such a manner to serve as a biomarker and employed as such by the BIB system 400. Example cases may employ many hundreds or thousands of contiguous pixels to create regions that may be referred to as "areas of interest", where the biomarkers that define this area may be referred to as a biomarker region or biomarker area.

The camera module 410 may be configured to capture images of, not only facial regions and facial subregions, but additional regions, such as exposed neck, shoulder, and even arm regions of an individual may be also acquired.

Digital pixel-size partitioning of these other regions may result in many more biomarkers and/or biomarker containing subregions to be provided via the DAA 410 as input into and processed by the present invention.

Figure 3:
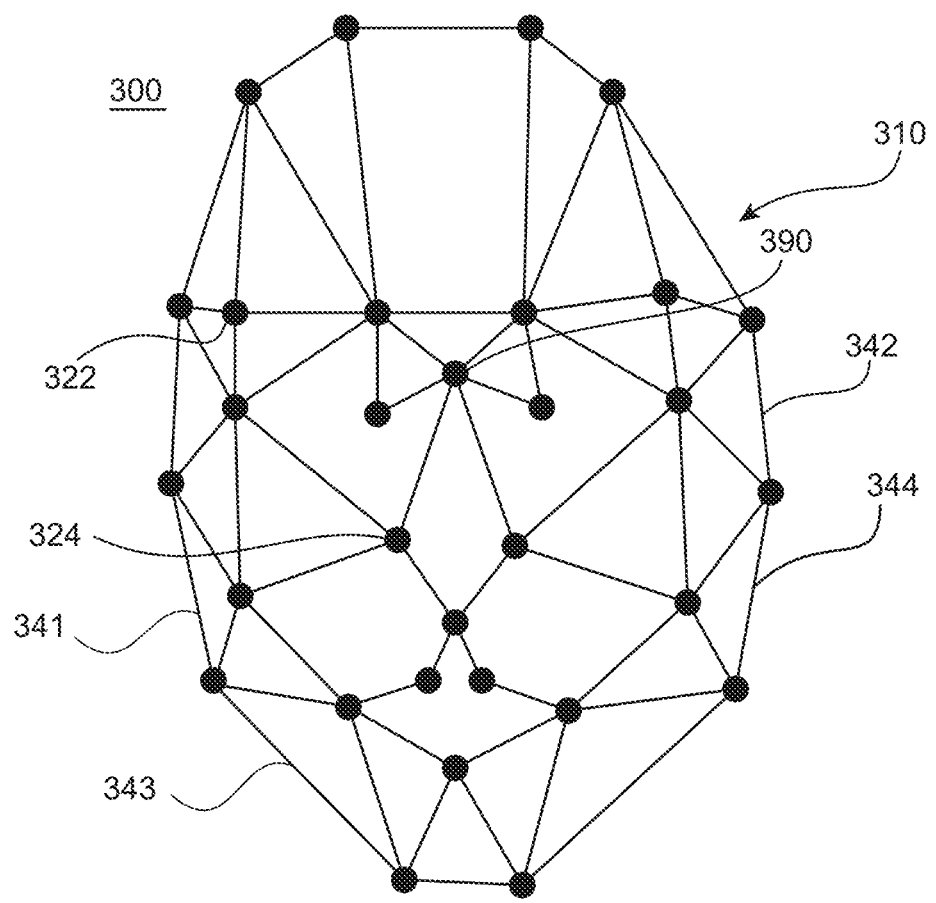
FIG. 3 represents a 2-dimensional diagram of spatially separated, biomarker-microregions shown with interconnecting lines between selected biomarkers, where the lines represent topological distances between or amongst the selected biomarkers.

FIG. 2 represents a head region 200 having spatially separated spot-size microregions. The head region 200 includes a facial region 210 and a neck region 263 of a test subject. The facial region 210 is shown with spot-size microregions 221, 224, 225, and 234, which may be spatially separated such that each spot-size element may be a biomarker. The entirety of external biomarkers shown in FIG. 2 represent a data set that may be configured by a Data Preprocessing Apparatus 420 and formatted into a 2-dimensional diagram of spatially separated, spot-size microregions represented in FIG. 3. The spot-size microregions have interconnecting linkages 341, 342, 343, 344 between selected spots, representing topological distances and vectors that separate the selected spots. At least one of the spots, for example spot 390, may be highlighted and depicted as a benchmark that may serve as a point of reference against which other biomarkers may be compared or assessed. Each biomarker can be defined in terms of a multicomponent, mathematically-expressed variable composed of; a qualitatively or quantitively established biologically-relatable parameter (P), a location (X, Y), and optionally a relative distance ($\Delta X$, $\Delta Y$), which may be established in space in frameworks of Cartesian or related polar coordinates, or other coordinate systems. In the case where polar coordinates may be used for mapping relationships between or amongst biomarkers, relative distances (ΔX, ΔY) and vector designators θ may be used by the present invention. The combined parameter, location variables, or variants, may take on a data format similar to (P, x, y) to facilitate data transmission between the DAA 410, the DAC 420, and the other parts of the BIB system 400. Thus, any benchmark may be expressed in terms of a biometric parameter P and a location x, y as a point of reference to a specific body region or spot. In similar light, any biomarker may be related to a benchmark by a biometric parameter P and relative separation distance (ΔX, ΔY), or by a biometric parameter P, a distance (ΔX, ΔY), and vector θ.

Figure 5:
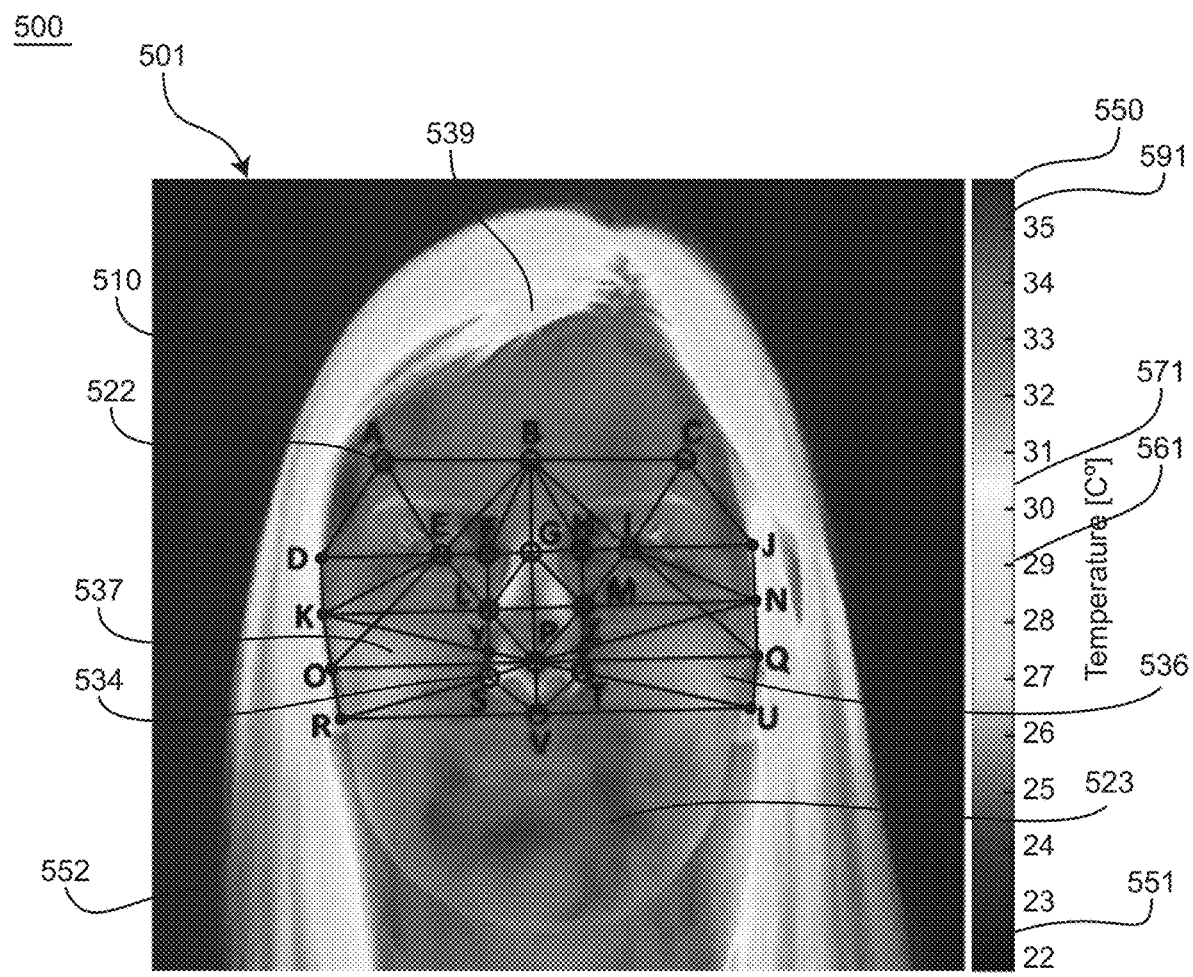
FIG. 5 represents a grayscale illustration of a contemporary infrared spectral thermal display of macroscopic facial regions having color-coded thermal regions.

The BIB system 400 may be a multifunctional biometric imaging apparatus that has been configured to produce a contemporary infrared spectral thermal display 500 of macroscopic facial regions having color-coded thermal regions as represented in FIG. 5 (FIG. 5 is a grayscale illustration of the infrared spectral thermal display 500). The thermal display 500 has a facial image 501 and a bar chart 550. The facial image 501 is a visible image represented by a full spectrum colorimetric rendering of the facial region 510 as well as a background region 552 that have been captured within the infrared (IR) region of the light spectrum. The bar chart 550 serves a means to calibrate temperature domains within the facial image 501 and enables approximate quantification of temperatures and temperature profiles. Temperatures are shown to span along a continuous spectrum in the bar chart 550 between a relatively cold region 551 through intermediate temperature regions 561 and 571 up to a maximal temperature 591. The background regions 552 correlate with the extreme cold region of the temperature spectrum. By comparison, facial regions 522 and 523 are shown to correlate with the upper extreme temperatures, while regions 536, 537, and 539 are depicted at intermediate temperatures 561 and 571.

Figure 6:
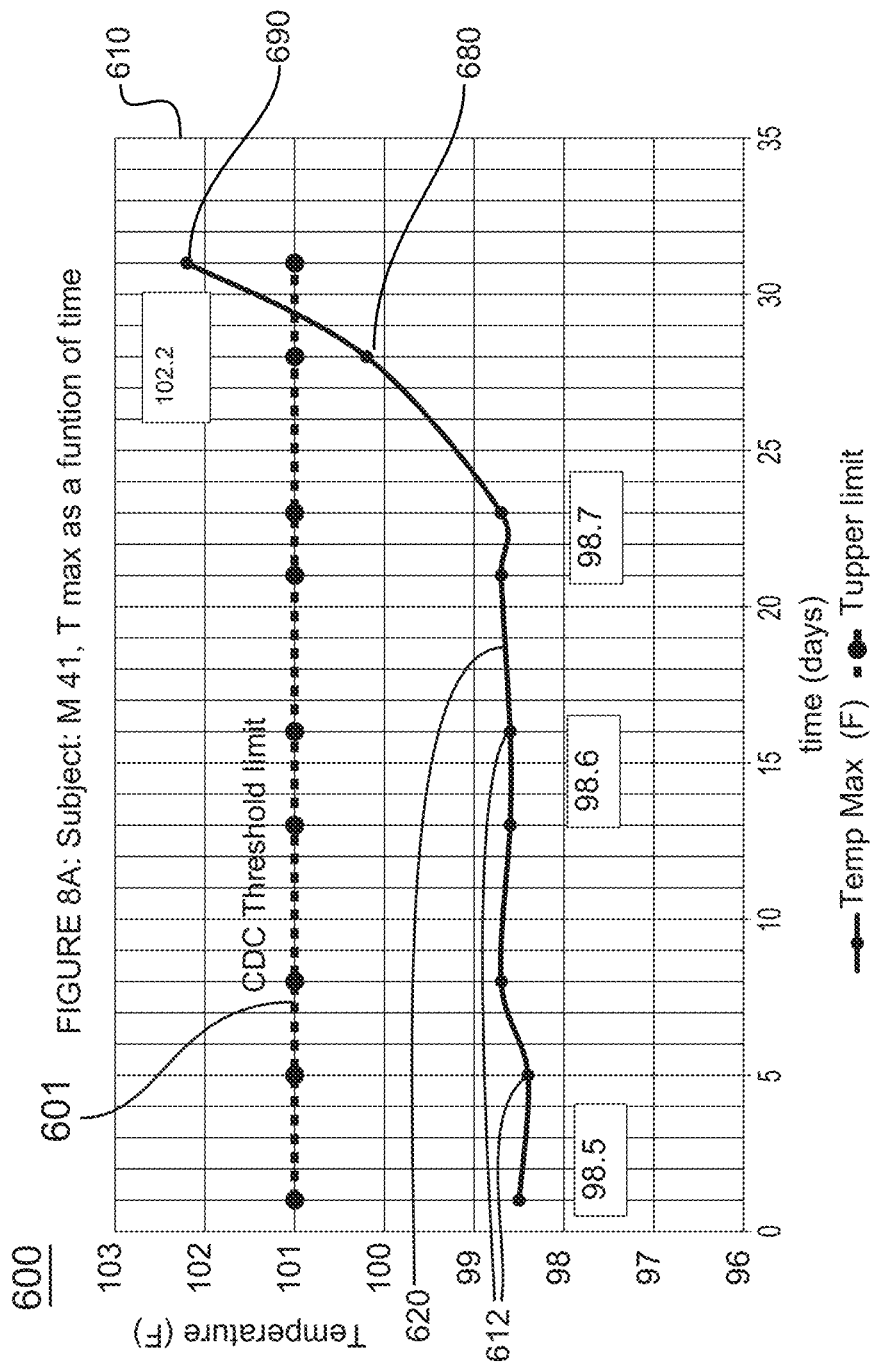
FIG. 6 represents a graphic illustration of time-based, maximal-measured temperatures of a hypothetical subject.

The BIB system 400 may be a multifunctional biometric imaging apparatus that has been configured to measure, record, process, and display temperature data associated with the facial regions of a test subject. FIG. 6 represents a graphic illustration 600 of temperatures of the test subject's facial regions shown in FIG. 5. The graph 610 in FIG. 6 is a plot of the maximal temperatures acquired on a weekly basis over a month-long period. The individual test subject temperatures were acquired by use of at least one of the cameras within the Data Acquisition subsystem 410 described in relation to FIG. 4. The test subject temperatures were quantified and graphically configured by algorithms employed by a combination of the SSI preprocessor 420 and the CPU 430, and then displayed on an appropriately configured display unit 442. While a multiplicity of spot sized micro-regions representing the highest temperature readings may be available and change in facial position at any time, the precise spot-size microregions (see 522 and 523 in FIG. 5) representing maximal temperatures were employed to create FIG. 6. These microregions are referred to as thermal biomarkers and thermal biomarker regions.

Overlaid on the graph 610 of FIG. 6 is a reference line 601 indicating a body temperature guideline established by the US Center for Disease Control (CDC). The values that exceed this CDC threshold limit are potential indicators of a serious fever situation within the test subject and may indicate the presence of a COVID-19 or related illness.

Commercially available devices measure temperatures such as those represented by the discrete data point 612 that may be displayed together with similar data in graphic form 610 in FIG. 6 upon manual collection of time-based data as represented by FIG. 6. These devices simply measure temperature(s) and most commonly employ a single determination of the maximal temperature at a particular point in time as an indicator of COVID-19 illness. Representing an above normal, illness-indicating temperature 690 along with a potentially actionable temperature 680 with values that may be produced by data provided by a conventional device are shown in FIG. 6. The temperature that may trigger concern may equate to a body temperature of 100.4 F at 680 and the uppermost range may equate to a high at 690 of 102.2 F in certain individuals under certain circumstances. A logical conclusion that an observer may make with awareness of the CDC guidelines and upon seeing the results presented by FIG. 6 is that the individual with temperatures above 100.4 F and above 102.2 F has a fever, is ill, may have COVID, and is likely to require immediate subsequent actions, such as medical follow-up, isolation, and/or entry prevention into a crowded space. Even with the present invention, if one were to rely upon single-point, maximal temperatures as the sole determinant of illness, erroneous conclusions of the type the CDC warns against (i.e., temperature-measurement-only devices are not medical devices and should not be used as an indicator of illness) are known to have occurred and may continue to occur at an alarming rate. Unfortunately, since an elevated temperature is not a definitive indicator of the illness, one is confronted with the option of avoiding use of non-contact temperature devices entirely or including other parameters within the test protocol to enable a more accurate illness diagnosis.

In contrast to conventional and commercially available devices in use for screening of COVID, the BIB system 400 not only acquires but also records and stores a plethora of temporal-based data that may be recalled and automatically compiled into a variety of trend analyses such as the one shown in FIG. 6. The graph 610 is comprised of data 612 simulating temporal variations of a test subject's temperature that has been measured on a regular basis over a period of about a month. Even with the addition of temporal-based data and corresponding trend analysis thereof to provide a medical diagnosis as discussed above, one may conclude in this case that the individual has become initially ill at point 680 and continued to get worse up to the point where the individual's temperature 690 far exceeded the CDC guidelines. Upon observing this extremely high temperature 690, one would conclude that the individual has become and is seriously ill. Unless due caution is taken, there is a likelihood that this conclusion may be in fact a "false positive" result, whereby this particular test incorrectly indicates that an illness (i.e., COVID-19) is present. The intelligent, self-learning features of the BIB system 400 enabled by the analytics, algorithms, and data processing 436 that are embedded within the SSI 432 of the Central Processing Unit 430 provide confidence and assurance that such as conclusion is not possible.

Figure 7:
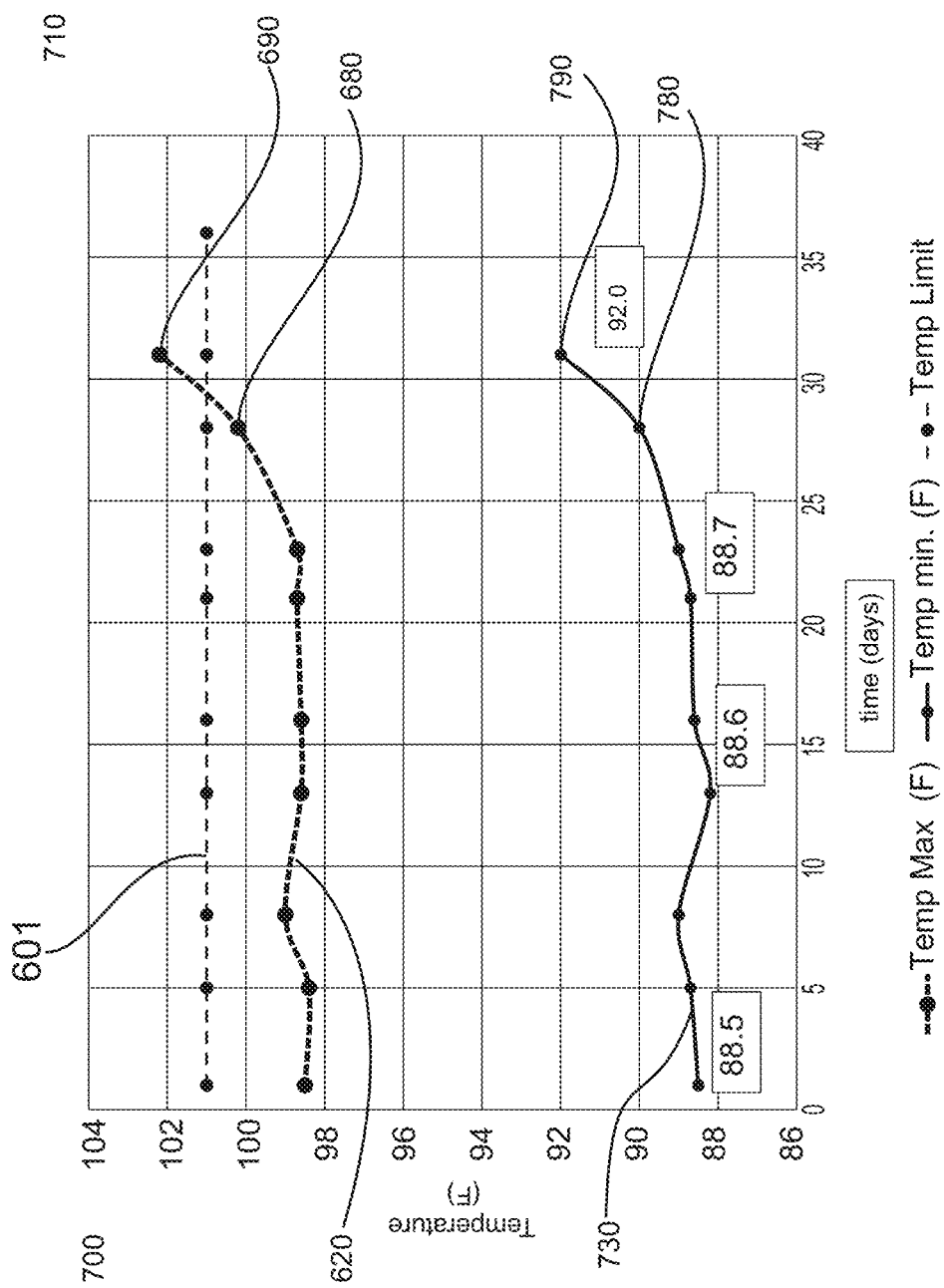
FIG. 7 represents a graphic illustration of time-based, maximal and minimal temperatures of a hypothetical subject.

FIG. 7 represents a graphic illustration 700 of time-based, maximal and minimal temperatures of a hypothetical test subject. The graphic illustration 700 includes the trend line 620 and the upper limit trend line representing a maximal temperature (Tmax) threshold 601 as described in relation to FIG. 6. The graphic illustration 700 also includes a trend line 730 representing the minimal temperature (Tmin) measured on the same test subject at the same times that the maximal temperature data 612 was acquired. Image digitization and preprocessing 420 of the facial image 510 and thermal profiling 550 as described in relation to FIG. 5 were used in part to generate the temperature data shown in FIGS. 6 to 9.

Comparison of the high temperature regions 680 and 690 of the Tmax trend line 620 to the corresponding data points 780 and 790 on the Tmin trend line 730 reveal a nearly identical upward movement during the last week of observation. The implication of this coordination between Tmax and Tmin trends can be explained by use of FIG. 8 and FIG. 9.

FIG. 8 represents a graphic illustration 800 of time-based, differential temperatures of a test subject. The graphic illustration 800 includes a graphical form 810 of a trendline 830 illustrating the time-based temperature differences (Delta T) of the Tmax trendline 620 shown in FIG. 6 minus the Tmin 730 trendline shown in FIG. 7.

Figure 9:
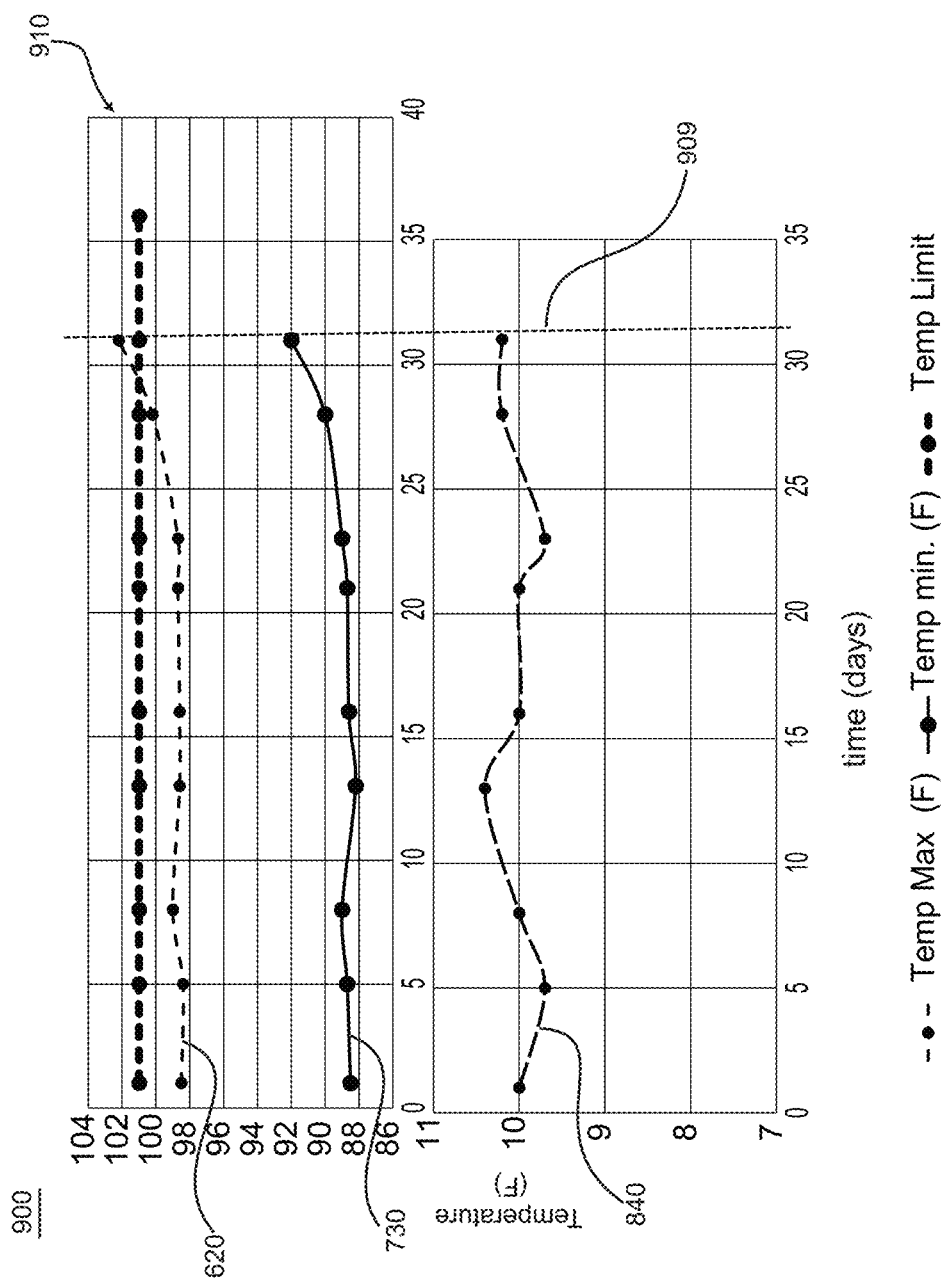
FIG. 9 represents a graphic illustration of an erroneous diagnosis derived from analytics using time-based temperatures of a hypothetical subject.

FIG. 9 represents a graphic illustration 900 of an erroneous diagnosis derived from analytics using time-based temperatures of a hypothetical subject. The graphic illustration 900 presented as a multiparameter graph 910 comprised of the Tmax trendline 620, and overlays of the Tmin trendline 730, the Delta T trendline 840, and an interconnecting vertical reference line 901 as described in relation to FIGS. 6 to 8. FIG. 9 provides insights into the type of erroneous conclusions that may be drawn from the earlier-described, exclusive usage of single-point or even temporal-based Tmax data. The near-mirrored behavior in the Tmax 620 and Tmin 730 trendlines when compared to the Delta T trendline 840 of FIG. 8 clearly reveals that the coordinated Tmax and Tmin upswings occur with no significant change in the difference between the temperature trends 620, 730. The comparison of the three trendlines in FIG. 9 reveals an important insight regarding the onset of the highest Tmax values. A (correct) conclusion may be that the observed T max values in this scenario may simply be an artifact that may be fully explained when one considers additional, and in this case, external (i.e., noise) factors. The Delta T data 840 is essentially constant throughout the period; thus, the Tmax and Tmin upswings are responding synchronously to an external stimulus, such as the individual having been temporarily acclimated to an unusually high environmental temperature, such as that one would experience waiting in long lines in a hot car for COVID-19 tests, working on a hot roof, running on a hot beach, and the like. Since Delta T is constant when normalized for environmental noise, the reasonable conclusion is that no significant subject-based change to the individual's health has occurred.

When the preliminary results shown in FIG. 9 are observed in a clinical setting, the validation of the conclusion is easily achieved by simply allowing the patient in this case sufficient time adjust to a new environmental setting and remeasure the suspect temperatures. Upon observing a near-simultaneous fall off of the Tmax and Tmin values, the individual can accurately be diagnosed as not affected by an abnormally high body temperature.

Figure 10:
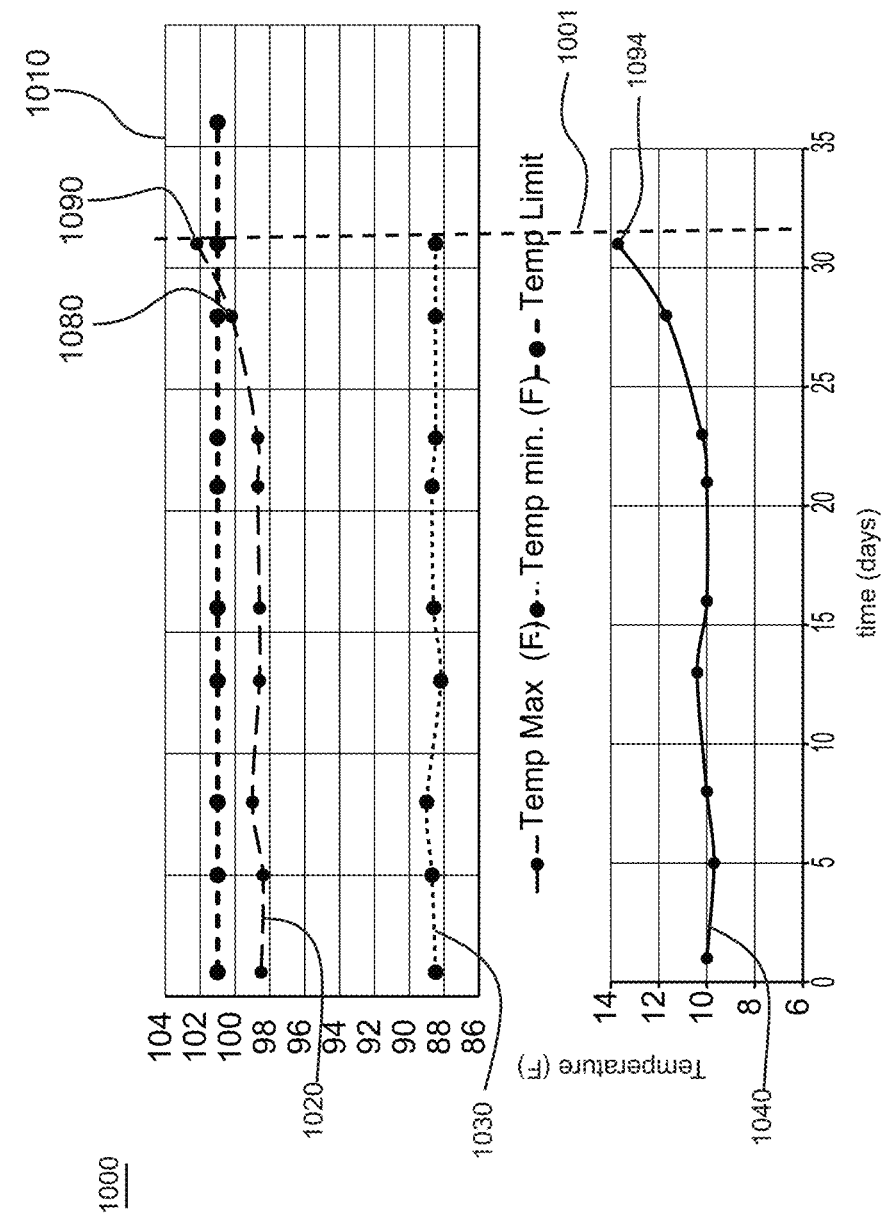
FIG. 10 represents a graphic illustration of a diagnosis derived from analytics using time-based temperatures of a hypothetical subject.

FIG. 10 represents a graphic illustration 1000 of a diagnosis derived from analytics using time-based temperatures of a test subject. The graphic illustration 1000 is representative of a potential medical diagnosis resulting from deployment of the analytics and algorithms 436 as described in relation in FIG. 4. The FIG. 1000 illustrates a unique capability of the BIB system 400. FIG. 10 provides a direct comparison to the earlier scenario put forth in FIGS. 6, 7, 8, and 9 and may serve to help illustrate a more correct diagnosis that may be an outcome of another diagnostic scenario derived from analytics using time-based temperatures by again considering the biomarkers (T max, T min, and Delta T) of the BIB system 400.

FIG. 10 is a 3-parameter thermal analysis in the form of a graphic illustration 1000 comprised of a Tmax trendline 1020, with overlays of a Tmin trendline 1030, the Delta T trendline 1040, and an interconnecting vertical reference line 1001. In this scenario the Delta T trendline 1040 mirrors the Tmax data uptrend 1020, while the Tmin trendline 1030 is essentially constant. The highest Tmax value 1090 may represent the presence of fever in the test subject and a true warning about this particular test subject's health.

The BIB system 400 may have at least one configuration that functions to collect and process Tmax biometric data and Tmin biometric data. The BIB system 400 calculates Delta T parameters by use of appropriately configured analytics and algorithms within at least one CPU. The BIB system 400 then evaluates the instantaneous, or alternatively the temporal-based, magnitudes of the Tmax, Tmin, and Delta T data. The BIB system 400 compares these magnitudes to pre-established, specified frameworks that serve as a decision matrix. The BIB system 400 has an intelligent processor to interpret, extract, and provide to a suitably configured display unit 442 with at least one graphic format such as the graphical illustration 900 as described in relation to FIG. 9, the graphical illustration 1000 as described in relation to FIG. 10, or in any suitable graphical format(s) representing the resultant product of the described processing, analyses, evaluation, and communication of a medical diagnosis.

The BIB system 400 may have at least two data acquisition apparatuses essentially the same as the data acquisition apparatus 410 described in relation to FIG. 4. Each of the at least two data acquisition apparatuses have a sensor 415 to sense and measure the local temperature of the surrounding area and communicate this data via a transmission line 4010 along with the acquired image thermal data 501 as described in relation to FIG. 5 to the preprocessor 420. The at least two DAAs may be disposed in a spatially separated arrangement. For example, a first DAA may be located at a first entry point to a workplace that may be adjoining and outside of an exterior door. The biometric parameters Tmax, Tmin, and Delta T of a test subject as previously described, along with an array of other biometric parameters which are fully described below, are initially acquired by cameras and/or sensors of the first DAA at an instant when an individual approaches and passes through the field of view of the first DAA. The first DAA may also receive, record, and/or otherwise react to a RFID tag, employee ID badge, or other identifying device carried by the individual and may transmit the related data to the preprocessor. A second DAA is located along the travel path of the test subject entering the workplace at a point inside of the entry door. A distance of between a few feet (preferably at least 1 yard) and as much as about 100 yards or more may separate the first DAA from the second DAA. The individual must pass both the first DAA and the second DAA such as in a hallway attached to an entryway where imaging and image capture operations by each of the DAAs can occur. The time to transit between the apparatuses may several seconds or several minutes or more. Upon image sensing and acquisition at the first DAA, the preprocessing apparatus 420 initiates a clock timer and sets the start time to a zero setting. Upon image sensing and acquisition at the second DAA, the preprocessing apparatus 420 utilizes the clock timer to determine and record the time interval relating to the time of the individual's travel between the first DAA and the second DAA. The preprocessor associates the start time with an initial set of temperatures, which is presented in a four-factor numerical format—Tmax(1), Tmin(1), Delta T(1), t(0)—to the preprocessor. The second data set having the same albeit updated data format—Tmax(2), Tmin(2), Delta T(2), t(2). The skin layer on the head, shoulder, and arm regions of an individual, and particularly the epidermal layer on the facial regions, respond nearly instantaneously to rapid environmental changes within which the individual experiences. These temporal-based changes in the epidermal temperature may provide insights into the health conditions of that individual.

Figure 11:
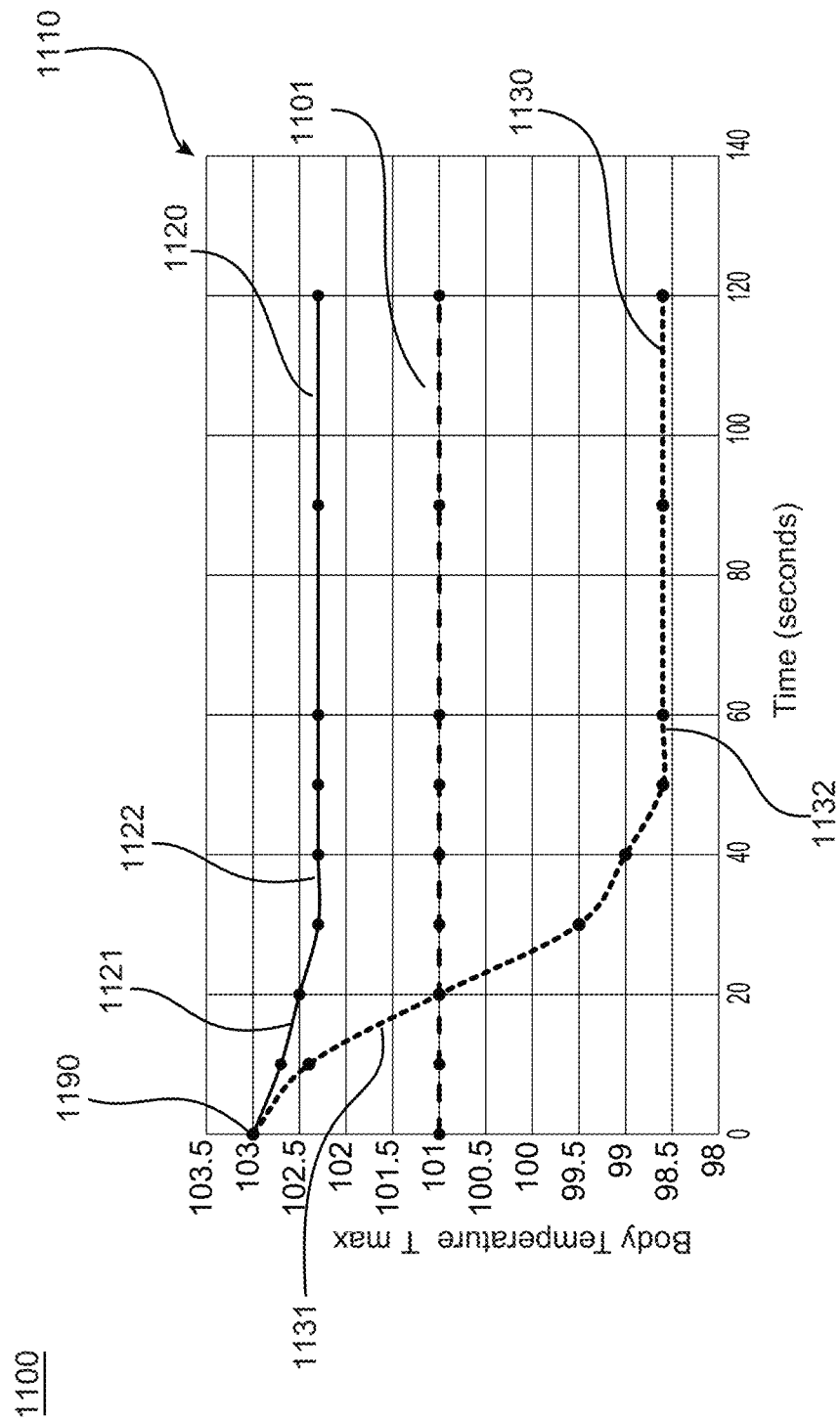
FIG. 11 represents a graphic illustration of time-based, differential temperatures of a hypothetical subject transiting through multiple temperature zones.

The biometric imaging and biotelemetry (BIB) system may perform an analytical and diagnostic method as described in relation to FIG. 11, which represents a graphic illustration 1100 of time-based, differential temperatures of a test subject transiting through multiple temperature zones. FIG. 11 illustrates in graphic form two thermal profiles 1120 and 1130 derived from measurements of the maximal facial temperatures (Tmax) of one individual known to be ill with a fever represent by thermal profile 1120 and similar measurements on a second but healthy individual represent by thermal profile 1130. The graph 1110 presents facial temperatures in relation to residence times of the two individuals upon short term exposure (i.e., from about 1 up to 120 seconds) to a temperature difference. Temperature and time data have been acquired, analyzed, and graphically reported during the individuals' movements through two separate, temperature zones wherein the entry point to each temperature zone is configured with a DAA 410 as described above. The DAAs 410 may be hard-wired by use of a fiber optic cable, a CAT5 or similar cable, a High-Definition Multimedia Interface HDMI cable such as described by 4010 and 4012 in relation to FIG. 4 or wirelessly connected directly with a preprocessing unit 420. Optionally, the DAAs may be connected indirectly to the preprocessor via an internet connection (not shown). The detailed graph 1100 in FIG. 11 employs real-time acquired environmental thermal data and further comprises biometric data representing two sets of maximal facial temperatures acquired by a pairing of at least two sets of DAAs 410 as described in relation to FIG. 4.

The first of the pair of DAAs is located at an exterior portal of a building into which both individuals enter. The first of the pair of DAAs registers and records an environmental temperature data point Tenv(1) (i.e., in this case at a value of 114° F.) and identifies and communicates this data to the preprocessor 420. The preprocessor 420 interprets and appropriately stores this data as the first entry into a yet unknown number of environmental temperatures that surround the designated localities. This data may serve as the initial learning element of the BIB system 400 upon start-up of the system.

The second of the pair of DAAs is located a short distance inside the portal area and resides in a relatively cold, air-conditioned entryway. The second DAA registers and employs the preprocessor 420 to record a second environmental temperature data point Tenv(2) equal to 70° F. which serves as the second learning element.

Upon initial startup of the BIB system 400, the Tenv(1) and Tenv(2) data serve to seed the self-learning process. This initial set of data is compared by use of preprogramed algorithms to an array of comparative data that may be pre-loaded and stored within each DAA. If the preprocessor observes any anomalies at this stage as it proceeds through the early self-learning and self-checking activities, a signal may be sent to the system controller to restart, to recalibrate, and then reassess the preliminary Tenv data. Once the system validates its self-calibration is correct and agreement of the early environmental data set with pre-established norm is confirmed, the system will proceed to acquire and analyze biomarker data.

The preprocessor then proceeds to perform an array of calculations, the first of which is to determine that mathematical difference between the interior Tenv(2) and the exterior Tenv(1) temperatures. In this case, the differential referred to as delta T(1) is determined to be 44° F. which is a variation in temperature that may be routinely encountered during the summer months in the US. The individuals successively approach and enter the external portal region within a short time period of each other and each independently enters the field of view of the first DAA. The first DAA acquires and records a data set for the individual consisting of biometric data—Tmax(1), Tmin(1), Delta T(1), t(1), along with the existing environmental temperature Tenv(1). Each individual having been exposed to, and has at least partially, equilibrated to the extreme external Tenv(1) temperature equating to 114° F. As each individual transits through the entryway and into the air-conditioned building, the second DAA acquires and records a data set for each individual consisting biometric data—Tmax(2), Tmin (2), Delta T(2), t(2), along with the environmental data Tenv(2). FIG. 11 illustrates the time-based thermal response of both individuals and provides in graphic form 1110 a comparison between an ill individual (i.e., one ill with a fever) and a healthy individual as each acclimates to the lower, interior temperature zone upon coming directly from a high temperature zone.

Individuals, including those who are ill and exhibiting a high fever, may respond nearly-instantaneously to a rapid change in environmental conditions. In FIG. 11, we observe that the Tmax(1) data 1190, which has been initially and instantaneously measured on both individuals, appear in the graph at the time-axis origin t(0) is shown as identical, overlapping values equating to 103° F. At this temperature, a concern may arise about the wellbeing of the individuals due to the fact that these temperatures exceed the 101° F. CDC guidelines. However, within a few seconds a significant divergence occurs between the maximal facial temperatures of the individuals. The ill individual responds to the environmental temperature change nearly immediately at 1121 as is the case with the healthy individual at 1131. The individuals' data are communicated to the preprocessor subsystem 420 which calculates the rates of change for each individual. Results as shown at 1122 and 1132 in FIG. 11. A full graphic portrayal 1110 of the entire data set may also be transmitted to and displayed upon on a suitably configured display unit 442 within the System Controller Unit (SCU) 440. A difference in the rate of change may be calculated by the preprocessor 420 between the ill and healthy individuals and may appear, for example as the regions 1121 and 1131 in FIG. 11. Importantly, the thermal response behavior of the ill individual is shown to rapidly drop (i.e., within a few seconds) to an approximate steady-state temperature 1122 which lands significantly above the threshold level representative of a fever 1101. In contrast, the thermal response behavior of the healthy individual likewise rapidly drops (i.e., within a few seconds) to an approximate equilibrium temperature level 1132 reaching a value significantly below the threshold level representative of a fever 1101. FIG. 11 illustrates a diagnostic method of the present invention comprising a unique capability to employ facial thermal biomarkers to differentiate ill from healthy individuals and to serve as a symptom-specific screening diagnostic apparatus. The biometric imaging and biotelemetry system in this light provides a system and method for delivering highly accurate medical diagnoses, while at the same time significantly reducing, or eliminating, the diagnostic errors that are common with today's commercially available products.

In a recent experiment designed to illustrate the dynamics of the previously described rapid-response effect upon a subject transitioning throughout significantly different temperature zones, the following method and sequence of events was conducted and recorded:

1) the facial temperature Tmax (1) was acquired and recorded on a healthy test subject after residing comfortably for 30 minutes in a room environment of 68 F;

2) the test subject then travelled into a full sun-exposed environment and rested comfortably, where after 15 minutes a second facial temperature Tmax (2) was measured and recorded, the Tmax (2) value was found to be 7.2° F. above the Tmax (1) temperature;

3) the test subject then returned to the original room environment where a time-dependent set of Tmax biometric data points were acquired and recorded; and 4) the findings reveal that after 60 seconds of re-entry into the room environment, the individual's facial temperature recorded as Tmax (3) fell to within 1 degree of the starting Tmax (1) value and after 300 seconds the facial temperature, recorded as Tmax (4) was equal to that at the start of the experiment. These results lend evidentiary support to the scenarios discussed in FIG. 11.

Figure 12:
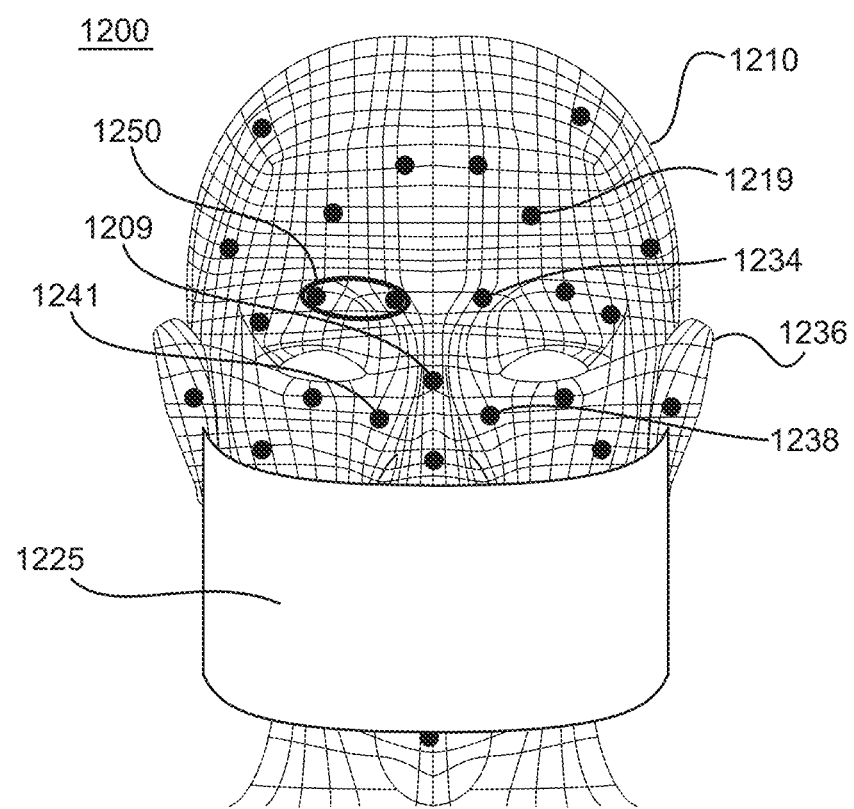
FIG. 12 represents an illustration of spatially separated, biomarker-microregions with a large portion of the facial region obscured by a mask covering.

The biometric imaging and biotelemetry (BIB) system may have an analytical and diagnostic method to accommodate the large variations that may occur in subject images acquired by a DAA 410. Facial masks are commonplace in response to today's health crisis where the inter-person transmittance of the highly contagious COVID-19 virus is widespread. FIG. 12 represents an illustration 1200 of spatially separated, biomarker-microregions with a large portion of the facial region obscured by a mask covering. FIG. 12 is used to illustrate the impact that a facial mask 1225 has upon non-contact bioimaging devices. Facial mask 1225 may be an N95 mask, an N95 respirator, or equivalent. Such a mask is in common use today by a large portion of the population and in some situations may be legally mandated. The mask 1225 serves as an air-way, particulate-filtering facepiece respirator that meets the U.S. National Institute for Occupational Safety and Health recommendations for personal air filtration. The mask 1225 is capable of filtering nearly all airborne particles and is worn as a covering on the mouth and nose regions of an individual's face. As shown in FIG. 12, the mask 1225 when worn correctly covers approximately the lowermost third of the individual's face. Unfortunately, the mask 1225 fully obscures the biomarkers in this region and thus removes a significant portion of the biomarkers from direct observation by the camera(s) 411, 412, 413, and 414 and/or sensor(s) 416 of the DAA(s) 410. By use of intelligent data processing and uniquely configured algorithms within the preprocessor subsystem 420 that enable AI-based decision processes, the BIB system 400 recognizes the presence of a mask 1125 and optionally may make adjustments in the data acquisition and inter-subsystem transmittance processes to accommodate this obscurant. Upon recognition of a mask, the preprocessor 420 may communicate via interconnection(s) 4020 and 4030 the presence and type of obscurant directly to a system administrator, a medical professional, a security guard, or the like via a user interface and/or display. Optionally, the mask may communicate via real-time communications 4012 to deliver feedback or instructions to the subject by use of an audio or visual display 417. Feedback instructions to the subject may request the individual to temporarily remove the mask and position appropriately for additional image-capture processes.

Alternatively, the protocols preprogrammed within and administered by the BIB system 400 may make adjustments (also referred to "fine tuning") to the DAA image capture devices and data processing processes to accommodate loss of some facial biomarkers due to masks and a wide array of other facial or head, neck and shoulder obscurants.

The biometric imaging and biotelemetry (BIB) system may have an imaging system capability and method of real-time intelligent recognition of obscurants where the obscurants negatively impact the image and/or biometric data acquisition processes. Upon recognition, the preprocessor subsystem 400 functions in concert with predefined algorithmic protocols to trigger immediate remedial adjustments to be made that accommodate a wide range of obscurants while providing a highly accurate medical diagnosis.

The biometric imaging and biotelemetry (BIB) system may be a multifunctional biometric imaging apparatus that has been configured to measure, record, process, map, and track thermal biomarker regions associated with the facial regions of a subject. Any selected number of individual, contiguous biomarkers (for example, hundreds or thousands or more) may be grouped to form a biomarker subregion.

In FIG. 12, the facial image 1210 has a subregion 1250 that has been configured to comprise a large number of individual, mostly contiguous pixels to create a biomarker region. The 2-dimensional, projected area of this particular subregion has been calculated, recorded, and pinpointed as an area of interest as a result from a thermal-based diagnostic analysis and related outcome produced by the BIB system 400. The subregion after several measurements of Tmax exhibited a Tmax range between 99.0° F. and 99.8° F. While these levels fall below the established CDC guidelines and are generally not of concern, they may represent a pending issue and/or may suggest a presence of an asymptomatic condition. A noteworthy capability of the BIB system 400 is the capability to identify and to earmark a subregion for re-evaluation. Such a subregion is exampled as the subregion 1250 depicted in FIG. 12. After close tracking and subsequent re-evaluations of the Tmax parameter associated with this area over a time period, it may be observed that the projected area expands in a statistically significant manner (for example by 100% to 200%) over the measurement period during which the range of Tmax values is observed to also be increasing by for example a range that averages about 0.5° F. However, because no single Tmax value has exceeded the CDC guidelines and few, or no, existing devices have this capability, little attention may be brought to these observations and an individual exhibiting these behaviors may be unaware of a pending issue. Furthermore, the rate of expansion (for example expressed as +darea/dt) of the projected area of the subregion along with any increases in Tmax (dTmax/dt) and the rate of contraction (for example expressed as —darea/dt) along with any changes in Tmax of subregion may be precisely measured and mathematically expressed. Executable algorithms 436 within the CPU 430 are configured to perform a variety of such calculations relating to these disclosed rates. In addition, the algorithms within the CPU 430 are configured to calculate the second derivative of these parameters (for example, which may be expressed in general terms as (dp/dt)/dt, where "p" designates a parameter of interest and may be selected from the listing of parameters 1585 in FIG. 15. A second derivate may be used to quantify and characterize the acceleration in expansion or contraction of a projected area of a subregion; and thus, provide insights into the acceleration/deacceleration of a diagnostically relevant parameter.

It is precisely with deployment of these unique analytics that diagnoses of asymptomatic or pre-symptomatic conditions may be forthcoming as it is unknown at the present time what, if any, non-invasive tests can relate nearly normal temperature trends to the presence of a worrisome virus, or other illness, in an individual.

The biometric imaging and biotelemetry (BIB) system may provide a multifunctional biometric imaging method that has been configured to perform the following operations: 1) to acquire and utilize image data from a facial region of an individual; 2) to measure, select, and assign an initial set of biomarker data to the image; 3) to identify and select a subset of contiguous, or nearly contiguous biomarkers and establish a boundary area within which the selected biomarkers fall and where a preselected biometric parameter such as Tmax is essentially constant over the area at the time of initial selection; 4) to uniquely identify by use of a suitable mathematically effective term that enables tracking of that area as a biomarker subregion; 5) to remeasure and record a biometric parameter associated with the selected area, such as Tmax over a period of time; 6) to remeasure, quantify, and record the area of the defined subregion along with consideration of the selected biometric parameter(s), their rates of change and acceleration trends; and 7) to evaluate and report on the extent and trends of change occurring within the selected parameter (i.e., Tmax as exampled) and the encompassing area (i.e., Tmax/dt as exampled). A potential noteworthy capability of the BIB system 400 to function as a medical research device that may help uncover a novel means of diagnosing asymptomatic or pre-asymptomatic individuals that may be impacted by at least one unknown illness via utilization of a vast array of biometric parameters that may be observed on the macroscopic scale, on the microscopic scale, or both.

In FIG. 12, a mask 1225 positioned in such a manner to cover the lowermost regions, such as inclusive of the mouth, chin, and nose of an individual's head 1210. The mask 1225 blocks this region along with the biomarkers contained in the region (the region is representative example of a biomarker subregion) that is in this case obscured from viewing by one or more of cameras 411 and 412 and camera lenses 413 and 414 disposed within the DAA 410. The interface 405 within the DAA 410 is configured to communicate a data and information set which may reveal the obscurant and pin point obscured regions to the preprocessor 420 via a data pathway 4010. The preprocessor may optionally communicate an instruction set to the at least one lens unit 413 and 414 via a set of actionable commands through a data pathway 4012, which serve to trigger adjustments within at least one of the lens members 413 and 414, and which may be configured to make focal, spectral, field of view adjustments, or combinations. Upon making the prescribed lens adjustments, the preprocessor 420 may trigger the DAA 410 that has been configured with adjusted, presumably optimized, lens members to capture a follow-on set of image data to ascertain if a problem(s) may persist with facial region obscurants. In the case where a retest of a mask-covered facial region does not improve the image characteristics and/or quality of the characteristic face-image, the preprocessor may communicate this scenario directly (via an in-series configured channel, such as 4020 interconnected with 4030) to the system controller subsystem 440 for display of this as an image-obscured condition to the system administrator, to a medical professional, to a security guard, or the like, who may choose to take action in response to the information provided by the BIB system 400. In a further option that is provided by the present invention is an instruction set that may be delivered in real time to the test subject via a data channel 4012 originating at the preprocessor 420 and may terminate in an audio or visual output device 417 configured within the DAA subsystem 410 for such individualized instruction(s). An instruction may be provided to the individual, for example, as an audio or written request to temporarily remove the mask, and once the mask is temporarily removed, to re-engage the DAA subsystem for reimaging. Alternatively, an instruction to proceed to enter a building, an instruction to wait for arrival of a personal assistant, or combinations of these instructions may be issued to the test subject.

In FIG. 12, a large portion of the facial area obscured by a mask 1225, there is an adequate number of biomarkers 1219, 1241, 1234, 1236, and 1238 that may be acquired by the DAA, and then analyzed and archived by the preprocessor 420 and employed by the central processor 430 to construct and deliver a successful and reliable medical diagnosis. In so doing, at least one of the biomarkers may serve as a point of reference to which distances separating and angular vectors relating to selected other biomarkers may be established and quantified and in so doing represent compound biomarkers that may be used in a variety of medical diagnoses. The positional and spatial arrangement of biomarkers provides the preprocessor and/or the central processing subsystem with at least two data framework options. The biomarkers may be formatted by use of a Cartesian coordinate system wherein each biomarker is precisely located within a 2-dimensional framework and may take on a generic X, Y or a dx, dy data pairing. Alternatively, the biomarkers may be formatted by use of a polar coordinate framework wherein each biomarker is located within a generally circular shaped framework and may take on a generic X, $\theta$ or a dx, d$\theta$ data pairing. The angle theta ($\theta$) may be employed in reference to a pre-established horizontal plane, a vertical plane, a polar- or circular-configured plane or combinations. Likewise, the biomarkers may then be formatted into a Gaussian function to distribute arbitrary constants and recalibrate biomarkers through a variety of mathematical functions to achieve highest level of diagnosable accuracy.

The biometric imaging and biotelemetry (BIB) system has a capability provided by the DAA 410 to acquire at least one image of the entire macroscopic facial region of an individual by use of high-resolution digital imaging 411 which enables the acquired image to be decomposed into many microscopic subregions (see FIG. 2, e.g. 224, 225, 234, and 250), that in turn can be digitized by a suitable integrated circuit such as a custom ASIC 409 that employs a sensor (not shown), for example a Complementary Metal-Oxide-Semiconductor, CMOS sensor. The number of microscopic regions, referred to as pixels, can fall into the range of a million to many millions and is limited primarily by the resolution of the camera. For example, the ArduCAM 5 MP (2592×1944) camera from ArduCAM with an ArduCAM Sensor OV5640 may easily generate 5 million pixels (1.4 micron×1.4 micron). The 8MP Sony IMX219 Sensor Camera can generate approximately 8 million pixels. The Sony Prosilica Model GT 6400 CMOS-based camera may routinely generate 31,400,000 pixels from a single image by use of a 6480×486 framework operating at 3.8 frames per second. Digital camera technology is rapidly advancing and newer models are becoming available that may generate more than 40 million pixels from a single digital image. A multimillion-pixel image transmitted from the DAA 410 to the preprocessor 420 supplies the preprocessor with an abundance of options from which to compile an initial selection set, referred to as a biomarker set.

In FIG. 12, the spatial distance between biomarker 1219 (which resides at a point just below the individual's hairline and in a clear, unobstructed view of the DAA) and the reference biomarker 1209 may be determined and may have a unique value (designated as dx19, dy19) as a calculation result from the interactions of the data acquisition functions of the DAA 410 combined with data processing algorithms and analytics of the intelligent, self-learning preprocessor 420 and in certain cases with data processing algorithms and analytics provided by the intelligent self-learning CPU 430. The spatial distance dx19, dy19 is calculated and recorded at a time when the subject individual initially encounters and is analyzed by the BIB system 400. The initial spatial distance may be associated with the length of the forehead brow when in a relaxed position that may stem from a relaxed emotional or physiological state of the individual. At a time 25 hours later, when the individual encounters the BIB system 400 once again, such as in the case where an employee enters the same workspace through the same entry portal the following day, a second acquisition of the dx19, dy19 biomarker is recorded at a second time 25 hours later than the initial base-time. A significant decrease (by approximately −30%) in the spatial span distance of the dx19, dy19 biomarker is detected indicating a large change in the brow furrow that is the cause of a large, and easily noticeable forehead wrinkle to emerge. At this point, this observation may simply be an indicator of stress. A vast number of other biometrics 1570 may be used by the system AI, analytics, and algorithms to enhance the accuracy of a pending diagnosis. For example, the system may employ facial colorimetric-based biometrics 1592 such as those described in relation to FIG. 15.

A diagnosis may proceed in the following sequence: 1) the at least one of the digital acquisition apparatus 420 serves to acquire facial image data from a test subject over the visible color spectrum; 2) the image data is communicated to the preprocessor 420; 3) the preprocessor serves to transpose the image data into digital machine augmented data which is comprised of at least a facial topographic map of selected biomarker subregions along with the entire, or selected portions of a corresponding mapping of the facial subregions using the coded colorimetric data that is configured to be recognized and operationally managed by the central processor 430; 4) the preprocessor then communicates 4020 the coded colorimetric transposed data as a data stream to the CPU 430; 5) where upon receiving the coded colorimetric data, the CPU proceeds to employ an AI-based decision algorithm 436 to generate a mapping of, and analysis of the colors that are preselected as being relevant to the diagnosis under consideration; 6) the CPU enters the selected data into designated data fields of at least one algebraic equation and proceeds to execute at least one mathematical calculation; and then 7) upon completion, the CPU generates at least one result and communicates this in the form of a data stream to a suitable display 442 for observation and interpretation by a system user. The resultant data stream may optionally be directed to an encoder/decoder unit 433, a central storage member 438 an interface unit 444 and transmitted to any suitably configured accessory 450 or external processor/storage member 490.

The biometric imaging and biotelemetry (BIB) system may have a capability to not only measure physical dimensions of a candidate biomarker subregion, but also has a capability to determine a color of a subregion or portions of subregions. In FIG. 2, the extreme width of an individual's nose may be measured by simply calculating the distance between biomarkers 224 and 234, whose precise locations have been established by the DAA 410 and preprocessor 420. This dimension may be referred to as a maximal nose width see FIG. 15, 1593 (i.e., wn). An initial sequence of measurements taken from an individual over a period of time establishes a long-term characteristic, or base-line, nose width which is accessible to the system via a central storage member 438. During the same initial sequence of data acquisition events, the colors 1592 of the nose (i.e., CNL, CNR, and CNC) and other facial subregions are measured and recorded. Optionally, the density of any selected color may also be determined, analyzed, recorded, and employed as an additional factor(s) to enhance the accuracy of selected medical diagnoses.

During a subsequent data acquisition event, statistically significant variation in the nose width (wn) and coloration parameters 1592 may be observed, measured, and recorded for use in CPU calculation that may be deemed by the system's AI operations and/or from user directed instructions. An increase in the width of the nose in the range of 10% to 15% has been measured (e.g., designated as nasal flair) and along with a shift in nose color from a neutral flesh color to a deep reddish coloration. Changes in these biomarkers, once normalized for any obscurants that may be present, may be reliably used in conjunction with thermal biomarker data and related thermal analyses and in combination may provide further evidence of a virus infection related illness being present in the individual. Alternatively, the change in brow furrow properties as earlier cited serve to support the conclusion that the observed changes are simply stress related. It is clear, that the expanded capabilities of the present invention serving to capture and to operate with a vast number of biometric parameters are enablements of the system's objective of rendering highly accurate diagnoses correlating to a variety of simultaneous well-being studies.

The biometric imaging and biotelemetry (BIB) system may use coloration data to provide insights relating to an individual's wellness/illness conditions. Coloration data acquired on a macroscopic facial region of an individual 210 revealed a presence of a reddish discoloration of a side-forehead region 251 as illustrated in FIG. 2. The discolored subregion 251 may be defined as a topographic surface area bounded by biomarkers 250, 252, 253, and 254. A calculation performed by the preprocessor simultaneously processing thermal biomarker data establishes that the area of the discolored subregion to be approximately 1.5 square centimeters. These observations are combined with the intelligent preprocessor and CPU analytics to indicate that the thermal data reveals significant thermal abnormalities. An interim conclusion may be drawn that the individual is highly likely (see 1692 in FIG. 16) to be affected by a virial or flu-like illness. Other physiologic conditions are illustrated in the form of a table 1610 as shown in FIG. 16. An alternative subset of the suspected conditions 1690 may be examined and evaluated by the BIB system. For example, suspect ailments which correlate with hyperpigmentation 1690 may include; a rash, a sunburn, a bruise, eczema, or perhaps a more serious condition such as psoriasis, rosacea, or Sturge-Weber Syndrome. The BIB system 400 has capabilities to acquire colorimetric data along with a vast number of diagnosis-contributing data and via AI-based analytics and algorithms; and thus examine a large number of possibilities and statistically eliminate a portion of the possibilities from further consideration. The CPU may then proceed to further analyze the remaining options and by use of at least one algebraic calculation derive results that provide insights relating to an individual's wellness/illness conditions.

In FIG. 12, once the totality of data is processed through a series of diagnostic algorithms that consider a plethora of biomarker analyses and temporal-based changes, and taking into account for potential noise and obscurant variables that may influence an evaluation, the measured differences in selected biomarkers and comparatives of biomarkers with achieved data may serve as a critical and novel approach to medical diagnostics. Thus, we may observe from examples that the BIB system 400 capability is noteworthy even in the situations where large portions of the images may be obscured to generate accurate medical diagnoses. Given these capabilities, the likelihood of a "false-negative" or "false-positive" diagnoses is extremely low, and the potential for those outcomes that incorrectly indicate that a particular condition or attribute is absent drops to near zero.

A further example of the vast capabilities of the biometric imaging and biotelemetry (BIB) system can now be described with reference to FIG. 13, which is a tabulation 1310 of factors 1385 that may serve to obscure biomarkers and otherwise interfere with or complicate an image-based diagnosis. Configured within the data preprocessor 420 and the CPU 430 subsystems are data storage repositories 421 and 438, mathematical algorithms 421 and 436, data nodes 425 and 439 with transmission channels 4010, 4012, 4020, 4022, 4030, 4032, 4040, and 492 that collectively have been configured to support and efficiently execute a large number of calculations that utilize a vast, multifactor data set. Data sets inclusive of millions, or hundreds of millions, or even billions or more of data elements can be rapidly (within a few seconds) processed by the cited subsystems and algorithms. The factors 1385 which appear in the right-most column 1380 of FIG. 13 may represent potential, albeit suspicious and possibly unreliable, biomarkers that may be captured by the DAA 410 and encountered during calculation-based analyses and processes. Anyone of these factors 1385, also referred to as obscuring factors, may serve to confuse, complicate, or otherwise negatively impact upon the accuracy of an image-based analysis. Clearly, if a medical diagnosis that is characterized as having the highest accuracy that may be possible is to evolve, then each and every potential complicating factor such as those exampled as 1385 must be accounted for in the system procedures and processes used in creation of the diagnosis. The center-most column 1390 of the table 1310 serves to categorize the various factors 1385 in such a manner to facilitate the volume and process-order of calculations that the preprocessor 420 must perform. The totality of factors 1385 along with the categorizations 1390 may be encoded in such a manner to enable recognition and appropriate analyses of the impacts, which may result in some, if not all of the factors being discarded from further analyses. Those factors that are algorithmically deemed necessary to continue into subsequent analyses, including statistically-based analyses, may be tabulated and displayed in one or more report formats, displayed on locally-residing display units, and, optionally encoded and transmitted to a cloud unit for broader dissemination, additional remote processing and analysis, and/or storage.

The impacts of a facial mask 1225 upon initial biomarker selection and related data set-prioritization that the BIB system 400 addresses have earlier been disclosed. The facial mask falls into a category reflecting the fact that the mask 1225 is a non-permanent obscurant that is only of concern during the image acquisition period where it is worn by the individual and may be removed temporarily to enable a more encompassing DAA 410 operation to be performed. Other non-permanent and removeable obscurants 1360 comprise items such as caps, hats, scarfs, turtle necks, hoodies, eye glasses, sunglasses, and the like. An individual wearing a removable item and upon interacting with the DAA subsystem that has a capability to recognize the situation may be instructed to briefly remove such articles to facilitate or optimize the DAA operations. Other factors may be characterized and addressed by the processors and algorithms as noise variables 1370 that are likely to be out of direct control or influence by the system, but nonetheless have to be appropriately considered in order to construct the most accurate diagnosis. Not all obstructing factors interfere with or obfuscate an analysis. In fact, some, when intelligently selected and processed can facilitate the analysis and improve the diagnostic proficiency. For example, the presence of an eyelid ring, nose ring, or nose stud, which are commonly worn as a jewelry item 1227 by a significant portion of the public, may be deemed by the preprocessor 420 as a noise variable 1370 and thus recognize it as a non-organic adornment and may in most likelihood disregard this particular facial subregion from consideration as a worthwhile biomarker. In contrast, by use of a comprehensive, ever-expanding achieve coupled with intelligent process and self-learning enabled, in part by at least one preprogramed algorithm within the preprocessor 420 and/or within the CPU 430, the item 1227 may, more appropriately, view the item to be a permanent facial feature and thereby designate and employ the subregion as a valid biomarker. In some cases, the item 1227 may be selected and employed as reference biomarker 1209 due to the fact that is easy to recognize and its position on the face may be extremely stable over a long period of time It is clear that the volume of data and associated workload that the BIB system 400 must accommodate suggests that the BIB system has unique and vast capabilities and performance attributes to differentiate it from devices and products that may exist in the present art.

Figure 14:
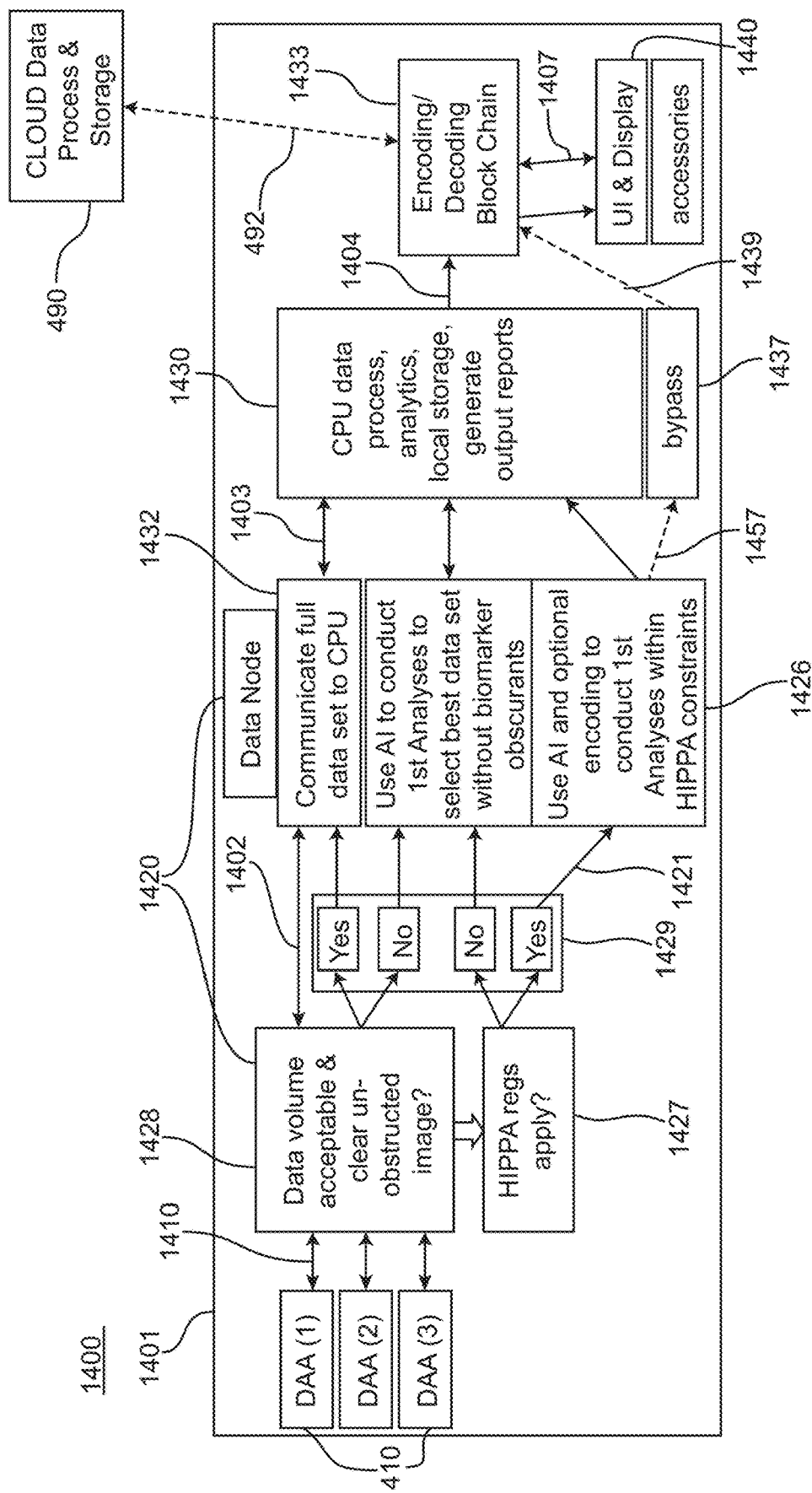
FIG. 14 represents a block diagram that employs a logic-tree format to illustrate data sources, data pathways, algorithms, analytics, AI enabled decisions and decision processes along with a sampling of executable actions performed by a biometric imaging and biotelemetry system.

Given that the types and impacts of obscurant factors have been described previously, FIG. 14 illustrates the data flows, algorithms, analytics and decisions that may occur within the framework of the BIB system 400. FIG. 14 is configured in the form of a logic-tree and block diagram 1401 that discloses a method of mapping of decision types and subsystem event-sequencing that may be employed by the BIB system 400. At least one DAA 410 may be positioned at an early point in the imaging process and serve to acquire image data from an individual (not shown) who is under assessment. At least one facial, neck, or upper shoulder image is acquired and converted into a suitable image digital format by at least one of the cameras 410 and ASIC assembly 409 that is specifically configured to perform this digitization operation. The ASIC(s) interact with an interface 405 to enable data transmission such that data is moved via a suitably designed interconnect unit 4010 configured to enable high speed data transmission. The preprocessor 1420 is configured to receive the image data stream and perform one or more of the listed operations: 1) it may convert image data into quantitative and/or qualitative biometric formatted digital data; 2) it may function to analyze, process, and/or transfer/retransfer the original and/or the reformatted data stream; 3) it may analytically process and render conclusions relating to the data; and 4) it may generate and issue system- or subsystem-actionable instructions to guide subsequent transfer and processing of the data.

In FIG. 14, data passes from the DAA(s) into and within the preprocessor subsystem (see 420 in FIG. 4). In some instances, the high-speed data transmission interface and/or interconnects may need high efficiency external and/or active cooling member (not shown) in order to accommodate the massive amounts of thermal energy generated by the massive data volumes and rates of transmission that are likely to be encountered. A double arrow is used in FIG. 14 to indicate that the data communications pathways may be two-way, also referred to as bi-directional channels where data, operational commands, instructions, analytical results, and the like, or combinations may flow in either direction between at least two interconnected subsystems. Upon receipt of the initial portions of the digitized image data in image data format by the preprocessor 420, the preprocessor serves to initiate and later will conduct as series of actions as it works to make and finalize a set of AI-based decisions. The preprocessor receives a near-continuous flow of data via a data pathway 1410 and undertakes the first set of considerations 1428 that must be addressed and then lead to actions that may be performed by the preprocessor 420. Examples of such considerations and resultant actions are: (a) establish a projection of approximately how much data is being input in real time; (b) what portion of the data represents a clear, unobstructed view of the subject; (c) how much of this data stream is to be achieved; (d) what accommodations within the various subsystem need to be made in order to accommodate the projections; and (e) assign unique biomarker identity to each data element within the selected set that will eventually be employed in pre- and post-processing operations. A further decision 1427 allocated to the preprocessor is to determine if the incoming data, or portions, may fall under that category of information comprising an individual's medical records and history, which are protected under the Health Insurance Portability and Accountability Act (HIPAA). In the event that the data, or a portion thereof is deemed by the preprocessor's 1420 evaluations to fall under HIPPA governance, this data may be segregated for special, and/or limited processing and transmission.

The BIB system 400 may be is configured to;

acquire image data from an individual by use of at least one DAA subsystem comprising at least one high resolution digital camera or sensor, transmit image data in the form of a digitized data stream to a preprocessor subsystem wherein the preprocessor serves to; receive the image-formatted data stream, employ at least one mathematical algorithm configured to interact with a data achieve, construct projections and preliminary conclusions which enable the preprocessor to assign actionable tasks relating to incoming data volume and quality, establish how much of this data stream is to be achieved, initiate and direct the achieving operation, determine subsequent operations and transmit an original and/or a reformatted data stream along with executable commands to the subsequent operation(s), assign unique biomarker identity to each data element within the selected set that will eventually be employed in pre- and post-processing operations, and determine if the incoming data, or portions thereof, may fall under that category of information comprising an individual's medical records and history, which are protected under the Health Insurance Portability and Accountability Act (HIPAA).

In FIG. 14, at least one data stream originates at the DAA 410 subsystem and is transmitted via one or more suitable configured interconnect(s) 1410 to the preprocessor subsystem 420. The preprocessor employs at least one data node and program algorithm, which employs a set of customized program software code to enable the preprocessor to fulfill certain preliminary operations. These preliminary operations include, but not limited to: evaluating the incoming data stream; in order to modify and/or reformat the incoming data stream as necessary; and to direct the output data stream to selected destination options where subsequent processing, determinations, and actions may be taken. The primary evaluations that preprocessor considers relate to data volume, data quality where some of the data may be impacted by the above-described obscurants 1385, and whether the data, or a portion thereof may be impacted by HIPPA regulations. The result of each consideration 1429 is in a binary form (i.e., yes or no) and upon establishing each result, the preprocessor performs an internal transfer (e.g., by use of interconnects 1422 and 1421) of the data along with an instruction set for subsequent handing of each designated data set. In the case wherein the incoming data is deemed to have no confounding issues, the preprocessor may simply transfer via a high speed data transfer link 1422 and 1432 the incoming data directly to the Central Processing Unit 430 wherein the CPU is configured to employ at least one data node 439 to arrange, configure, reformat, encode, and/or store some or all of the incoming data and along with custom program software-enabled analytic(s) to calculate by use of at least one custom software-enabled algorithm 436 a solution to a proprietary, complex mathematical equation that uses a multitude of variables in its solution determination.

Regarding HIPPA regulations and requirements to protect private and personal information, there are several cases that the preprocessor must address and render accurate judgements based on pre-programmed AI processes and self-learning protocols.

The first case is when the identity of the individual is known to the BIB system 400 and thus the system may be able to access at least one of that individual's medical profile(s) stored locally 421 and 438 within the BIB system 400, within a remote system (not shown), and/or via the cloud 490. In the second case, the identity of the individual may be unknown at the time of initial image capture, but may become known during early data acquisition and processing events. The third case is where the identity of the individual is, and remains unknown to the system.

Examples of the case wherein the identity of the subject individual is known may be represented by: 1) an employee using an employee ID badge to engage the imaging process to gain passage into a workplace; or 2) by a patient entering a physician's office for a medical appointment where upon arrival the patient is required to enter personal data via a digital interface display/keyboard device that is integrated with an automated registration processor/storage unit that alerts the medical staff to the readiness status of the patient.

In the case example where a patient enters a physician's office for a medical appointment, the BIB system 400 may be integrated into the medical patient's appointment log-in process by configuring the DAA 410 to capture image data and combine this with selected patient data to compile a patient profile reflecting the present state of wellness of the patient. When used in such a clinical setting where HIPPA regulations are strictly enforced, the BIB system 400 may draw upon a richer data set from which to establish a resulting diagnosis.

The BIB system 400 may be configured for in-clinic use. Specifically, the DAA subsystem 420 may be configured to have at least one contact sensor 416 selected from the group including a finger-contacting blood oxygen meter, a blood pressure sensor, a heart rate sensor, combinations, and the like. Combinations may be used that serve to generate tactilely-acquired biometric data and thus provides a richer data set from which to establish a resulting diagnosis.

In the situation where the individual's identity is unknown at the time of initial encounter and image capture, but afterwards or during which the identity, or portion, becomes recognizable resulting from interaction with the BIB system 400. An example of this may be the case where a minor child transits the imaging process accompanied by an adult parent when the parent is fully known to the system, a deduction may lead to a conclusion about the child's identity. In these cases, the image(s) and processed data along with any diagnoses that may result may be deemed by the preprocessor(s) to fall under HIPPA regulations and may require special consideration(s) that may include enhanced precautions and modified procedures that may employ AI-protocols to guide self-imposed limitations and/or other considerations upon the system. Thus, in this case, we observe from FIG. 15 that the image data stream 1410 and subsequent data transfer path 1421 for HIPPA impacted data may be diverted via a decision matrix 1429 to at least one of a specifically designated Specialized Synthetic Intelligence (SSI) embedded preprocessor 1426 and, optionally transfer past all, or most, of the central processor's analytic operations. The designated portion 1426 of at least one Specialized Synthetic Intelligence (SSI) capable preprocessor 1420 or of at least one Specialized Synthetic Intelligence (SSI) capable central processor 1430 may employ an AI-based algorithmic operation combined optionally with an encoding protocol that in cooperative arrangement have been specifically configured to protect an individual's personal and private information.

In the case where the individual's identity is and remains unknown to the system, or in some cases where there are no governing HIPPA considerations, for example in the case where a suitably executed HIPPA release document (that provides legally-binding authorization for use of the individual's personal and private information) has been entered on file and archived and/or accessible by the system, the data stream having an appropriately configured format may be linked 1402 by the preprocessor to pass directly by use of a suitable data pathway 1403 to the CPU 1430.

FIG. 15 represents a tabulation of factors that may be acquired in an initial form of image data then may undergo transformation and analytic processing during progression(s) through various subsystems of the inventive system. Selected sets of the factors disclosed in FIG. 15 are assembled and then employed to serve as parametric variables in at least one mathematical algorithm whose calculations' results are used to compile a medical diagnosis. The table 1580 of biomarker parameters 1570 that may be encoded for use as variables 1585 in the calculation(s) performed by the preprocessor 1420 operating in concert with the CPU 1430. The parameters 1570 may be grouped into categories 1590 that may facilitate subsequent statistical analyses, development of output reports and/or aid in archival operations. The parameters and related codes that are disclosed in FIG. 15 are exemplary and additional or alternate parameters may also be considered.

Upon receiving the data from the preprocessor, the CPU while working in concert with the preprocessor serves to analyze, prioritize, optimize, and select at least one data subset composed of encoded variables 1385 and 1585, and then to enter each selected variable into appropriate entry points (i.e., input data) of at least one mathematical equation. The number of variables upon which the mathematical equation(s) must be capable of employing is vast and from those disclosed in FIG. 13 and in FIG. 15, it is clear that the number of variables may fall in the range of at least 2 up to many hundreds, or more. The BIB System to acquire, process, store, and analyze vast amounts of data that may enable diagnosis of a wide array of physiological illnesses (for example, viral infections, influenza, COVID-19, stroke, lupus, rosacea, psoriasis, various other autoimmune diseases, and the like), under many routine circumstances it may be desired to place limitations on the data used for a particular analysis.

The BIB system 400 may be configured with a user interface, display, and controller (see 440 in FIG. 4) to enable an operator, who may be a clinician, a medical researcher, a system administrator, or the like to interact with a system. The operator may employ the user interface and display members to view the entire array of variables at any point in time that may be available for analysis. The operator may, by use of the locally-integrated controller unit 446, or optionally by a remote controller that provides access via an internet or cloud pathway 490 and 492 exercise discretion and/or preference over which variables may be of particular importance to an intended diagnosis. The operator may thusly select a subset of variables and by use of the user interface limit and designate a particular data subset where after the CPU proceeds to execute the algorithm(s) using the designated data subset and generate at least one solution to the complex, multifactor calculation(s). The system AI capabilities and/or operator may elect to examine other related diagnostic scenarios by making other data set selections. And upon the input of the alternate subset(s) of variables the CPU serves to recalculate results for every alternative predefined scenario or operator preference.

The BIB system 400 may have at least one mathematical equation configured to receive encoded biometric or other parametric data 1582 at predefined times and locations and upon deployment of the central processor 430 to confirm receipt of the data set and establish the sufficiency of the data set for the designated calculation(s) to proceed to employ the input data to execute at least one calculation, which may be in the form of a series of calculations and generate a numerical outcome of the calculation(s). The equation(s) may be defined as an "algorithm". The numerical outcome is compiled into a statistically derived probability factor relating to a designated illness or wellness. The use of a plurality of the afore-described biomarkers in at least one algorithm serves to aide in the development of medical diagnoses with enhanced confidence of the results.

To provide a clear and more consistent understanding of the specification and claims of this application, the following definitions are provided.

The term "exemplary" or "embodiment" is used to mean serving as an example, instance, or illustration. Any implementation or aspect defined as "example", "exemplary" or as an "embodiment" is not necessarily meant to be construed as preferred or advantageous over other aspects of BIB system.

The term "aspect" or "aspects" does not require that all aspects of the disclosure to be included in any of the described or discussed feature(s), advantage(s), or mode(s) of operation.

The term "contactless" and all its variations such as "non-contact", "non-contacting", and "without invasive contact" refers to a data gathering apparatus and methodology that employs a gap or spacing between the data gathering apparatus and the test subject or subjects. The gap is essentially asymptotic and may be in the range of 0.001 inches to 100 feet or more.

The term "about" refers to the statistical average variability as is typically found in the technology field of the BIB system and when used with a number or quantity is meant to have the same meaning as "approximate" or "approximately". Unless otherwise indicated, all numbers expressing quantities of ingredients, properties such as amounts or levels, and the like used in the specification and claims are to be understood as indicating both the exact values as shown and as being modified by the term "about". Thus, unless indicated to the contrary, the numerical values of the specification and claims are approximations that may vary depending on the desired properties sought to be obtained and the margin of error in determining the values. At the very least, and not as an attempt to limit the application of the doctrine of equivalents to the scope of the claims, each numerical parameter should at least be construed in light of the margin of error, the number of reported significant digits, and by applying ordinary rounding techniques.

The term "biomarker" refers to a physical feature, element, portion, or characteristic of a person or test subject that may be qualitatively or quantitively described. In some instances, it refers to a distinctive biological attribute or biologically derived indicator of a region, process, event, chemistry, or condition (such as aging, disease, or illness). The biomarker may in cases refer to a physical feature or to a physical dimension on a subject such as a single point, an area or region, or a spatial volume and may be of any size or shape. In addition, biomarker may refer to a measurable parameter or a quantifiable biological parameter that may serve as an indicator of a particular physiological state.

The term "external biomarker" refers to a biologic feature or parameter observable on the external surface of an individual that can be used as a point of reference or as a comparative benchmark or to measure a physiological state of a subject or relate to the presence or progress of disease or the effects of treatment.

The term "biometric" is intended to refer to at least one of: (a) the process by which a person's biomarkers are detected and recorded by an electronic device or system; (b) the measurement and analysis of unique physical, chemical, or behavioral characteristics; and/or (c) the analysis of biological data using mathematical and statistical methods.

The term "pixel" refers to the smallest discrete component of an image or picture.

The term "electrical communication" includes at least one of electrically connected and non-electrically connected: where electrically connected means components communicate with each other by means of a conducting path such as through a wire, a cable, other conductors, circuitry, combinations, and the like; and non-electrically connected means components communicate with each other with or without a conducting path such as with radio signals, lasers, cellular or other telephones, WIFI (wireless fidelity) or other wireless network protocols, satellites, combinations, and the like. Components with electrical communication may be both electrically connected and non-electrically connected; for example, components may be electrically connected to supply electrical power and non-electrically connected to transfer data and operating signals. The term "electrical communication" also includes when components are operatively connected to perform a particular function.

Unless the context clearly dictates otherwise, where a range of values is provided, each intervening value to the tenth of the unit of the lower limit between the lower limit and the upper limit of the range is included in the range of values.

The terms "a", "an", and "the" used in the specification claims are to be construed to cover both the singular and the plural, unless otherwise indicated or contradicted by context.

No language in the specification should be construed as indicating any non-claimed element to be essential to the practice of the invention.

Described methods can be performed in any suitable order unless otherwise indicated or contradicted by context.

Note that spatially relative terms, such as "up", "down", "top", "bottom", "right", "left", "beneath", "below", "lower", "above", "upper", and the like, may be used for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below", or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The simplified diagrams and drawings do not illustrate all the various connections and assemblies of the various components, however, those skilled in the art will understand how to implement such connections and assemblies, based on the illustrated components, figures, and provided descriptions.

While various aspects of the invention are described, it will be apparent to those of ordinary skill in the art that other embodiments and implementations are possible within the scope of the invention. Accordingly, the invention is not to be restricted except in light of the attached claims and their equivalents.

The invention claimed is:

1. A biometric imaging and biotelemetry system, comprising: a. at least one data acquisition apparatus that is comprised of a high-definition digital camera, a high-definition digital thermal camera, a sensor, a light source, a sound source, and a digital timer that are configured in mutual electrical communication and function synergistically to capture biometric data from a test subject; b. a preprocessor having electrical communication with the at least one data acquisition apparatus, where the preprocessor receives data in the form of a digital data stream and employs at least one arithmetic algorithm to perform a series of data analyses comprising calculating, comparing, and contrasting the biometric data in relation to at least one of archived data files inclusive of medical data files, programmed specifications, instructions, norms, and protocols; c. a central processor having electrical communication with the preprocessor, where the central processor receives data in the form of a digital data stream and processes the biometric data from the preprocessor and is configured with at least one of, high-performance computing, advanced mathematical algorithms, data translation algorithms, artificial intelligence, machine learning algorithms, a local data storage unit, electrical communication with at least one remote data storage unit, and block-chain encoding systems, whereby the central processor determines a subject-specific profile; and d. a controller unit having electrical communication with the central processor, the preprocessor, at least one data storage unit, and the at least one data acquisition apparatus, wherein the controller unit is configured to input, direct and control operations of and data flow between and amongst the central processor, the preprocessor, storage unit, and the at least one data acquisition apparatus, to construct, coordinate and consolidate analyses and subject-specific profile results from the interactions thereof, and to provide structure to the output of the central processor, of the preprocessor, and of the data acquisition apparatus, where the controller unit externally transmits the subject-specific profile.

2. The biometric imaging and biotelemetry system of claim 1, further comprising; a. a set of at least two data acquisition apparatus each configured with a high-resolution, digital, visible light camera and lens member, a high-resolution, digital, infrared thermal camera and lens member, at least one environment sensor, and at least one identification tag or badge reading sensor; b. at least one of a light source capable of delivering energy over a wide range of the electromagnetic spectrum to a test subject, a light intensity monitor, a light frequency monitor, a sound source, and a sound source monitor; c. at least one application specific integrated circuit; d. at least one block-chain protocol; e. an interfacing operating system with graphical user interface; f. an integration protocol; g. a set of interconnecting paths, where the interconnecting paths are at least one of wires, cables, ethernet cables, fiber optics, radio frequency transceivers, networking circuits, and application specific integrated circuits optionally configured into nodes or node clusters, and h. at least one digital display unit.

3. The biometric imaging and biotelemetry system of claim 1, configured in electrical communication with at least one of the central processor and the controller unit where a subject-specific profile inclusive of a medical diagnosis is displayed.

4. The biometric imaging and biotelemetry system of claim 1, where the biometric data is generated by time-lapse or continuous image capture of a large number of images from a large area of a test subject spanning a time period of from 0.01 milliseconds to about 5000 milliseconds and comprises at least one of a biomarker that is identified with a specific time-date stamp and corresponds to a region having an area on a test subject in the range of about 0.5 nanometers squared to 15000 nanometers squared.

5. The biometric imaging and biotelemetry system of claim 1, where the at least one biomarker is at least one of; a color-specific biomarker, a thermal-specific biomarker, a topography-related biomarker, a reflex-related biomarker, and a temporal-based change in at least one biomarker.

6. The biometric imaging and biotelemetry system of claim 1, where the at least one of, a camera, a sensor, a light source, a light intensity monitor, and a light frequency monitor of the at least one data acquisition apparatus serves to capture data from at least one portion of the electromagnetic spectrum inclusive of the infrared, ultraviolet, visible light and thermal spectral regions.

7. The biometric imaging and biotelemetry system of claim 1, where the preprocessor, application specific integrated circuit, and data acquisition apparatuses are in electric communication and employ at least one integration protocol (e.g. an advanced, custom mathematical algorithm) to process and analyze data directed at identifying and segregating portions of the biometric data from further processing when those portions fall short of meeting preestablished specifications.

8. The biometric imaging and biotelemetry system of claim 1, where the subject-specific profile is comprised of at least one of; parameters, groupings of parameters, data files, data matrices, video streams, at least one digitized data stream, mathematical functions, analytical conclusions, graphic relationships, operational instructions, and a medical diagnosis.

9. The biometric imaging and biotelemetry system of claim 1, where the at least two, data acquisition apparatus are configured in a spatially separated arrangement where a physical distance of, for example, about 2 to about 500 meters is used to separate the first of the two from the second of two to establish a time-delay between biometric data sets captured as a test subject moves from one of the data acquisition locations to the other wherein the digital timer is configured to measure and affix a time/date record thereof to each data set.

10. The biometric imaging and biotelemetry system of claim 1, where at least one of the preprocessor and the central processor recognizes the presence of an obscurant in the biometric data and is configured to make adjustments to the biometric data to accommodate the obscurant, or optionally, to deliver feedback to the test subject to remove the obscurant and proceed with data capture in the absence of the obscurant.

11. The biometric imaging and biotelemetry system of claim 1, where at least one of the preprocessor and the central processor is configured with at least one of analytics, algorithms, standards, programmed instructions, and electric communication with at least one data achieve to establish if the biometric data includes information protected under the Health Insurance Portability and Accountability Act and upon so determining to make accommodations for the subsequent data handling, transmitting, encoding, and reporting thereof.

12. The biometric imaging and biotelemetry system of claim 1, comprising at least one digital acquisition apparatus configured with at least one application specific integrated circuit and one mathematical algorithm to operate in collaboration to generate at least one digital data stream in the form of at least an image-configured data format and communicate same to the preprocessor comprising at least one of; an application specific integrated circuit, a node, a node cluster, a mathematical algorithm, and an artificial intelligent embedded processor, where the preprocessor further serves to receive and transpose the incoming data stream into a format suitable for subsequent mathematical digital processing, and where the transposed data suitable for mathematical digital processing may be defined as digitized, machine augmented biomarker data is transmitted to the central processor for analytical analysis, construct of at least one health profile by artificial intelligence methodologies, and delivery in the form of at least one medical diagnostic report to at least one graphic user display.

13. The biometric imaging and biotelemetry system of claim 1, where at least one of the preprocessor subsystem and the central processor further comprises a software-based program that provides a capability to transform, to intelligently analyze and to store data as prescribed by at least one programmed algorithm, and to make rational decisions reflective of at least one of characteristics and trends within the data stream, and to direct at least a portion of the transposed data onto data pathways for designated, secondary analytical processing by a central processing subsystem that is configured to draw intelligent conclusions from the calculation results, generate detailed and summary reports, manage and direct subsequent data and report outputs to at least one pathway interconnecting the central processor with block-chain based encoding and decoding protocols for user interface devices and accessories and for local or remote storage.

14. The biometric imaging and biotelemetry system of claim 1, where the at least one data storage unit serves as an archive for and a recipient of emerging medical symptomology data, system generated data, system learning scenarios, operating commands, system change records, specifications, norms, and protocols.

15. A biometric imaging and biotelemetry method, comprising: a. deploying at least one first data acquisition apparatus configured with at least one sensor member that serves to recognize the presence of a test subject and to initiate the subject-specific data acquisition processes; b. deploying at least one first data acquisition apparatus located in a first location configured to capture a first biometric data set from a test subject and converting it to a first digital data stream; c. deploying a digital timer to generate and affix a complementary data set comprised of time and date data to the first data stream; d. deploying at least one second data acquisition apparatus located in a second location removed from the first location where the second digital acquisition apparatus is configured to capture a second biometric data set from the same test subject and converting it to a second digital data stream; e. deploying a digital timer to generate and affix an additional data set comprised of time and date data to the second data stream; f. communicating the data streams to at least one of the preprocessor, the central processor, the controller, and a local or remote data archive; g. performing at least one of calculating, comparing, and contrasting the combined biometric data from the data streams in relation to at least one of archived data files, programmed specifications and instructions, norms, protocols, including self-learned and self-generated protocols, artificial-intelligence-based algorithms, and in so doing establish the sufficiency of data quality and quantity for processing continuation; h. performing at least one of interrupting the process should the analytic determination deem that further data acquisition may be needed, generating commands from the controller to initiate at least one additional local storage unit, data capture sequence, managing and analyzing subsequent data capture processes inclusive of initiating supplemental or alternate light sources, alternate sound sources, or both to thereby secure a satisfactory data set; i. initiating commands to enable process resumption; j. processing the qualified biometric data with at least one of high-performance computing, advanced mathematical algorithms, data translation algorithms, artificial intelligence, machine learning algorithms, local data storage, remote data storage, and block-chain encoding system; k. determining a subject-specific profile;
  l. determining a subject-specific medical diagnosis; and
  m. transmitting the subject-specific profile and medical diagnosis to at least one of, a graphic display device, a cloud-based storage member, and to the internet for further conveyance.

16. The biometric imaging and biotelemetry method of claim 15, further comprising deploying at least of, a light source, a sound source, a light monitor, a sound monitor to deliver to the test subject additional or alternate light, sound stimuli, or both to improve the data or data capture process, to provide a preconfigured reflex stimulus intended to trigger a reflex reaction, or both.

17. The biometric imaging and biotelemetry method of claim 15, further comprising deploying at least one external reflex stimulus and deploying the at least one digital image capture apparatus to capture at least one triggered response exhibited by the test subject in real time and to generate and include this data set as a biomarker within the captured data set.

18. The biometric imaging and biotelemetry method of claim 15, further comprising recognizing the presence of an obscurant in the biometric data, making adjustments to the biometric data, to the subsequent data acquisition process, or both, to thereby secure a satisfactory data set to enable a highly accurate subject-specific health profile and related medical diagnosis.

19. The biometric imaging and biotelemetry method of claim 15, further comprising deploying at least one of one of high-performance computing, advanced mathematical algorithms, data translation algorithms, artificial intelligence, machine learning algorithms, local or remote storage archives, and block-chain encoding systems to establish if the captured biometric data includes information protected under the Health Insurance Portability and Accountability Act and thusly enable isolation of that data segment and alignment of subsequent data transmission with governmental guidelines.

20. A biometric imaging method, comprising: a. acquiring image data from an individual by use of at least one data acquisition apparatus subsystem having at least one of a high-resolution digital camera and a sensor; b. transmitting image and sensor data in the form of a digitized data stream to a preprocessor subsystem, where the preprocessor serves to receive the data acquisition apparatus-formatted data stream and employ at least one mathematical algorithm configured to interact with a data achieve; and c. constructing projections and preliminary conclusions, which enable the preprocessor to i. assign actionable tasks relating to incoming data volume and quality, ii. establish how much of this data stream is to be achieved, iii. initiate and direct at least one data achieving operation, iv. determine subsequent operations and transmit at least one of an original data stream and a reformatted data stream along with executable commands to the subsequent operation, v. assign unique biomarker identity to each data element within the selected set that will eventually be employed in pre- and post-processing operations, vi. determine if the at least a portion of incoming data may fall under that category of information including an individual's medical records and history, which are protected under the Health Insurance Portability and Accountability Act, and vii. deploy block-chain based encoding, as deemed required. d. generating a test subject specific health profile based upon the totality of biomarker data that has been gathered, validated, and employed, inclusive of long- and short-period temporal variations, if any, deriving conclusions in the form of a medical diagnosis and transmitting all, or designated portions thereof, to at least one of; a user interface, a system monitor, an archive storage, a cloud-based computing facility providing remote data storage and/or processing services, and an internet connected recipient.

* * * * *